US010127647B2

(12) United States Patent
Forutanpour et al.

(10) Patent No.: US 10,127,647 B2
(45) Date of Patent: Nov. 13, 2018

(54) METHODS AND SYSTEMS FOR DETECTING CRACKS IN ELECTRONIC DEVICES

(71) Applicant: ecoATM, LLC, San Diego, CA (US)

(72) Inventors: Babak Forutanpour, San Diego, CA (US); Jeffrey Ploetner, San Diego, CA (US)

(73) Assignee: ecoATM, LLC, San Diego, CA (US)

( * ) Notice: Subject to any disclaimer, the term of this patent is extended or adjusted under 35 U.S.C. 154(b) by 98 days.

(21) Appl. No.: 15/130,851

(22) Filed: Apr. 15, 2016

(65) Prior Publication Data

US 2017/0301078 A1    Oct. 19, 2017

(51) Int. Cl.
  *G06T 7/00*   (2017.01)
  *G06T 7/60*   (2017.01)
  *G01N 21/88*  (2006.01)
  *G06T 7/13*   (2017.01)

(52) U.S. Cl.
  CPC .......... *G06T 7/0004* (2013.01); *G01N 21/88* (2013.01); *G06T 7/0085* (2013.01); *G06T 7/13* (2017.01); *G06T 7/60* (2013.01); *G06T 2207/20061* (2013.01); *G06T 2207/30108* (2013.01)

(58) Field of Classification Search
  CPC ....... G06T 7/00; G06T 7/0002; G06T 7/0004; G06T 7/13; G06T 7/0085; G06T 7/60; G06N 21/88
  See application file for complete search history.

(56) References Cited

U.S. PATENT DOCUMENTS

| 3,808,439 | A | 4/1974 | Renius |
| 4,248,334 | A | 2/1981 | Hanley et al. |
| 4,519,522 | A | 5/1985 | McElwee |
| 4,715,709 | A | 12/1987 | Sekine et al. |
| 4,821,118 | A | 4/1989 | Lafreniere |
| 4,870,357 | A | 9/1989 | Young et al. |

(Continued)

FOREIGN PATENT DOCUMENTS

| CN | 1365479 A1 | 8/2002 |
| CN | 2708415 A1 | 7/2005 |

(Continued)

OTHER PUBLICATIONS

International Search Report and Written Opinion dated Oct. 3, 2017, in International Application No. PCT/US2017/027476, 16 pages.

(Continued)

*Primary Examiner* — Sean Motsinger
(74) *Attorney, Agent, or Firm* — Perkins Coie LLP

(57) ABSTRACT

Systems and methods for detecting cracks in an electronic device are disclosed. In one embodiment, the method includes receiving an image of a front side of a mobile device and automatically identifying edges in the image. For given edges among the identified edges, the method includes determining whether another edge among the identified edges is present within a predetermined distance of the given edge. Next, straight line segments corresponding to the edges for which another edge is within the predetermined distance are identified, and then a crack evaluation assessment is assigned to the mobile device based at least in part on the identified straight line segments.

21 Claims, 8 Drawing Sheets

(56) References Cited

U.S. PATENT DOCUMENTS

| | | |
|---|---|---|
| 4,878,736 A | 11/1989 | Hekker et al. |
| 4,927,051 A | 5/1990 | Falk et al. |
| 4,951,308 A | 8/1990 | Bishop et al. |
| 5,027,074 A | 6/1991 | Haferstat |
| 5,077,462 A | 12/1991 | Newell et al. |
| 5,091,773 A | 2/1992 | Fouche et al. |
| 5,105,149 A | 4/1992 | Tokura |
| 5,216,502 A | 6/1993 | Katz |
| 5,280,170 A | 1/1994 | Baldwin |
| 5,319,459 A | 6/1994 | Mochizuki et al. |
| 5,339,096 A | 8/1994 | Beaufort et al. |
| 5,419,438 A | 5/1995 | Squyres et al. |
| 5,436,554 A | 7/1995 | Decker |
| 5,570,920 A | 11/1996 | Crisman et al. |
| 5,572,444 A | 11/1996 | Lentz et al. |
| 5,610,710 A | 3/1997 | Canfield et al. |
| 5,717,780 A | 2/1998 | Mitsumune et al. |
| 5,747,784 A | 5/1998 | Walter et al. |
| 5,775,806 A | 7/1998 | Allred |
| 5,839,058 A | 11/1998 | Phillips et al. |
| 5,920,338 A | 7/1999 | Katz |
| 5,949,901 A | 9/1999 | Nichani et al. |
| 5,965,858 A | 10/1999 | Suzuki et al. |
| 5,966,654 A | 10/1999 | Croughwell et al. |
| 5,987,159 A | 11/1999 | Nichani |
| 5,988,431 A | 11/1999 | Roe |
| 6,029,851 A | 2/2000 | Jenkins et al. |
| 6,041,229 A | 3/2000 | Turner |
| 6,181,805 B1 | 1/2001 | Koike et al. |
| 6,228,008 B1 | 5/2001 | Pollington et al. |
| 6,259,827 B1 | 7/2001 | Nichani |
| 6,264,104 B1 | 7/2001 | Jenkins et al. |
| 6,330,354 B1 | 12/2001 | Companion et al. |
| 6,330,958 B1 | 12/2001 | Ruskin et al. |
| 6,393,095 B1 | 5/2002 | Robinson |
| 6,462,644 B1 | 10/2002 | Howell et al. |
| 6,529,837 B1 | 3/2003 | Kang |
| 6,535,637 B1 | 3/2003 | Wootton et al. |
| 6,573,886 B1 | 6/2003 | Lehtinen et al. |
| 6,587,581 B1 | 7/2003 | Matsuyama et al. |
| 6,596,684 B2 | 7/2003 | Casagrande et al. |
| 6,633,377 B1 | 10/2003 | Weiss et al. |
| 6,667,800 B1 | 12/2003 | Larsson et al. |
| 6,754,637 B1 | 6/2004 | Stenz |
| 6,758,370 B2 | 7/2004 | Cooke et al. |
| 6,798,528 B1 | 9/2004 | Hartman |
| 6,822,422 B2 | 11/2004 | Sagawa |
| 6,842,596 B2 | 1/2005 | Morii et al. |
| 6,854,656 B2 | 2/2005 | Matsumori |
| 7,069,236 B1 | 6/2006 | Tsunenari |
| 7,076,449 B2 | 7/2006 | Tsunenari et al. |
| 7,178,720 B1 | 2/2007 | Strubbe et al. |
| 7,234,609 B2 | 6/2007 | DeLazzer et al. |
| 7,251,458 B2 | 7/2007 | O'Connell |
| 7,268,345 B2 | 9/2007 | Schultz |
| 7,334,729 B2 | 2/2008 | Brewington |
| 7,520,666 B2 | 4/2009 | Pevzner et al. |
| 7,567,344 B2 | 7/2009 | LeBlanc et al. |
| 7,646,193 B2 | 1/2010 | Suzuki et al. |
| 7,649,450 B2 | 1/2010 | Campion et al. |
| 7,702,108 B2 | 4/2010 | Amon et al. |
| 7,735,125 B1 | 6/2010 | Alvarez et al. |
| 7,761,331 B2 | 7/2010 | Low et al. |
| 7,783,379 B2 | 8/2010 | Beane et al. |
| 7,881,965 B2 | 2/2011 | Bowles et al. |
| 8,010,402 B1 | 8/2011 | Sharma et al. |
| 8,019,588 B1 | 9/2011 | Wohlberg et al. |
| 8,025,229 B2 | 9/2011 | Hammond et al. |
| 8,031,930 B2 | 10/2011 | Wang et al. |
| 8,107,243 B2 | 1/2012 | Guccione et al. |
| 8,112,325 B2 | 2/2012 | Foy et al. |
| 8,195,511 B2 | 6/2012 | Bowles et al. |
| 8,200,533 B2 | 6/2012 | Librizzi et al. |
| 8,254,883 B2 | 8/2012 | Uchida |
| 8,266,008 B1 | 9/2012 | Siegel et al. |
| 8,423,404 B2 | 4/2013 | Bowles et al. |
| 8,463,646 B2 | 6/2013 | Bowles et al. |
| 8,718,717 B2 | 5/2014 | Vaknin et al. |
| 8,743,215 B1 | 6/2014 | Lee |
| 8,824,136 B1 | 9/2014 | Interian et al. |
| 9,043,026 B2 | 5/2015 | Lien et al. |
| 9,582,101 B2 | 2/2017 | Chang et al. |
| 9,595,238 B2 | 3/2017 | Won |
| 2001/0039531 A1 | 11/2001 | Aoki |
| 2002/0014577 A1 | 2/2002 | Ulrich et al. |
| 2002/0035515 A1 | 3/2002 | Moreno |
| 2002/0067184 A1 | 6/2002 | Smith et al. |
| 2002/0087413 A1 | 7/2002 | Mahaffy et al. |
| 2002/0129170 A1 | 9/2002 | Moore et al. |
| 2002/0157033 A1 | 10/2002 | Cox |
| 2002/0162966 A1 | 11/2002 | Yoder |
| 2002/0186878 A1 | 12/2002 | Hoon et al. |
| 2003/0006277 A1 | 1/2003 | Maskatiya et al. |
| 2003/0036866 A1 | 2/2003 | Nair et al. |
| 2003/0061150 A1 | 3/2003 | Kocher |
| 2003/0146898 A1 | 8/2003 | Kawasaki et al. |
| 2003/0170529 A1 | 9/2003 | Sagawa |
| 2003/0197782 A1 | 10/2003 | Ashe |
| 2003/0204289 A1 | 10/2003 | Banerjee et al. |
| 2004/0012825 A1 | 1/2004 | Tesavis |
| 2004/0114153 A1 | 6/2004 | Andersen et al. |
| 2004/0141320 A1 | 7/2004 | Bock et al. |
| 2004/0150815 A1 | 8/2004 | Sones et al. |
| 2004/0156557 A1 | 8/2004 | Van Der Weij |
| 2004/0156667 A1 | 8/2004 | Berger et al. |
| 2004/0186744 A1 | 9/2004 | Lux |
| 2004/0205015 A1 | 10/2004 | DeLaCruz |
| 2004/0235513 A1 | 11/2004 | O'Connell |
| 2004/0242216 A1 | 12/2004 | Boutsikakis |
| 2004/0262521 A1 | 12/2004 | Devitt et al. |
| 2005/0027622 A1 | 2/2005 | Walker et al. |
| 2005/0128551 A1 | 6/2005 | Yang |
| 2005/0139661 A1 | 6/2005 | Eglen et al. |
| 2005/0143149 A1 | 6/2005 | Becker et al. |
| 2005/0167620 A1 | 8/2005 | Cho et al. |
| 2005/0187657 A1 | 8/2005 | Hashimoto et al. |
| 2005/0216120 A1 | 9/2005 | Rosenberg et al. |
| 2005/0222690 A1 | 10/2005 | Wang et al. |
| 2005/0231595 A1 | 10/2005 | Wang et al. |
| 2005/0240958 A1 | 10/2005 | Nguyen et al. |
| 2006/0167580 A1 | 7/2006 | Whittier |
| 2006/0184379 A1 | 8/2006 | Tan et al. |
| 2006/0195384 A1 | 8/2006 | Bauer et al. |
| 2006/0217152 A1 | 9/2006 | Fok et al. |
| 2006/0229108 A1 | 10/2006 | Cehelnik |
| 2006/0235747 A1 | 10/2006 | Hammond et al. |
| 2006/0261931 A1 | 11/2006 | Cheng |
| 2006/0271431 A1 | 11/2006 | Wehr et al. |
| 2006/0279307 A1 | 12/2006 | Wang et al. |
| 2006/0280356 A1 | 12/2006 | Yamagashi |
| 2007/0013124 A1 | 1/2007 | Graef et al. |
| 2007/0057815 A1 | 3/2007 | Foy et al. |
| 2007/0129906 A1 | 6/2007 | Stoecker et al. |
| 2007/0133844 A1 | 6/2007 | Waehner et al. |
| 2007/0140310 A1 | 6/2007 | Rolton et al. |
| 2007/0150403 A1 | 6/2007 | Mock et al. |
| 2007/0205751 A1 | 9/2007 | Suzuki et al. |
| 2007/0263099 A1 | 11/2007 | Motta et al. |
| 2007/0269099 A1* | 11/2007 | Nishino ............... G06T 7/0004 382/141 |
| 2007/0281734 A1 | 12/2007 | Mizrachi |
| 2008/0004828 A1 | 1/2008 | Mizrachi |
| 2008/0027581 A1 | 1/2008 | Saether et al. |
| 2008/0033596 A1 | 2/2008 | Fausak et al. |
| 2008/0097770 A1 | 4/2008 | Low et al. |
| 2008/0109746 A1 | 5/2008 | Mayer |
| 2008/0111989 A1 | 5/2008 | Dufour et al. |
| 2008/0149720 A1 | 6/2008 | Colville |
| 2008/0177598 A1 | 7/2008 | Davie |
| 2008/0207198 A1 | 8/2008 | Juric |
| 2008/0231113 A1 | 9/2008 | Guccione et al. |
| 2008/0255901 A1 | 10/2008 | Carroll et al. |
| 2008/0256008 A1 | 10/2008 | Kwok |
| 2008/0281691 A1 | 11/2008 | Pearson et al. |

(56) References Cited

U.S. PATENT DOCUMENTS

| | | |
|---|---|---|
| 2008/0296374 A1 | 12/2008 | Gonen et al. |
| 2008/0303915 A1 | 12/2008 | Omi |
| 2008/0306701 A1 | 12/2008 | Zhong et al. |
| 2009/0051907 A1 | 2/2009 | Li et al. |
| 2009/0078775 A1 | 3/2009 | Giebel et al. |
| 2009/0079388 A1 | 3/2009 | Reddy |
| 2009/0095047 A1 | 4/2009 | Patel et al. |
| 2009/0184865 A1 | 7/2009 | Valo et al. |
| 2009/0190142 A1 | 7/2009 | Taylor et al. |
| 2009/0207743 A1 | 8/2009 | Huq et al. |
| 2009/0244285 A1 | 10/2009 | Chathukutty |
| 2009/0247133 A1 | 10/2009 | Holmen et al. |
| 2009/0251815 A1 | 10/2009 | Wang et al. |
| 2009/0262341 A1 | 10/2009 | Konopa et al. |
| 2009/0265035 A1 | 10/2009 | Jenkinson et al. |
| 2009/0299543 A1 | 12/2009 | Cox et al. |
| 2009/0312009 A1 | 12/2009 | Fishel |
| 2009/0321511 A1 | 12/2009 | Browne |
| 2010/0005004 A1 | 1/2010 | Hudak et al. |
| 2010/0063894 A1 | 3/2010 | Lundy |
| 2010/0088192 A1 | 4/2010 | Bowles et al. |
| 2010/0110174 A1 | 5/2010 | Leconte |
| 2010/0115887 A1 | 5/2010 | Schroeder et al. |
| 2010/0147953 A1 | 6/2010 | Barkan |
| 2010/0157280 A1 | 6/2010 | Kusevic et al. |
| 2010/0161397 A1 | 6/2010 | Gauthier et al. |
| 2010/0169231 A1 | 7/2010 | Bowles et al. |
| 2010/0185506 A1 | 7/2010 | Wolff |
| 2010/0219234 A1 | 9/2010 | Forbes |
| 2010/0228676 A1 | 9/2010 | Librizzi et al. |
| 2010/0235198 A1 | 9/2010 | Fini et al. |
| 2010/0237854 A1 | 9/2010 | Kumhyr et al. |
| 2010/0262481 A1 | 10/2010 | Baker et al. |
| 2011/0035322 A1 | 2/2011 | Lively |
| 2011/0043628 A1 | 2/2011 | Yun |
| 2011/0060641 A1 | 3/2011 | Grossman et al. |
| 2011/0067520 A1 | 3/2011 | Ihrke et al. |
| 2011/0235853 A1 | 9/2011 | Bowles et al. |
| 2011/0313840 A1 | 12/2011 | Mason et al. |
| 2012/0016518 A1 | 1/2012 | Saario et al. |
| 2012/0029985 A1 | 2/2012 | Wilson et al. |
| 2012/0030097 A1 | 2/2012 | Hagan et al. |
| 2012/0054113 A1 | 3/2012 | Jayaraman et al. |
| 2012/0063501 A1 | 3/2012 | Aguren |
| 2012/0078413 A1 | 3/2012 | Baker, Jr. |
| 2012/0116928 A1 | 5/2012 | Gventer et al. |
| 2012/0116929 A1 | 5/2012 | Gventer et al. |
| 2012/0117001 A1 | 5/2012 | Gventer et al. |
| 2012/0127307 A1 | 5/2012 | Hassenzahl |
| 2012/0146956 A1 | 6/2012 | Jenkinson |
| 2012/0191562 A1 | 7/2012 | Bowles et al. |
| 2012/0235812 A1 | 9/2012 | De Mello et al. |
| 2012/0254046 A1 | 10/2012 | Librizzi et al. |
| 2013/0006713 A1 | 1/2013 | Haake et al. |
| 2013/0034305 A1* | 2/2013 | Jahanshahi ........ G06K 9/00624 382/201 |
| 2013/0046611 A1 | 2/2013 | Bowles et al. |
| 2013/0046699 A1 | 2/2013 | Bowles et al. |
| 2013/0124426 A1 | 5/2013 | Bowles et al. |
| 2013/0126741 A1 | 5/2013 | Srivastava et al. |
| 2013/0144797 A1 | 6/2013 | Bowles et al. |
| 2013/0155061 A1* | 6/2013 | Jahanshahi ............ G06T 15/00 345/419 |
| 2013/0173434 A1 | 7/2013 | Hartman |
| 2013/0181935 A1 | 7/2013 | McKenzie et al. |
| 2013/0191236 A1 | 7/2013 | Bowles |
| 2013/0198089 A1 | 8/2013 | Bowles |
| 2013/0198144 A1 | 8/2013 | Bowles |
| 2013/0226679 A1 | 8/2013 | Bowles |
| 2013/0246212 A1 | 9/2013 | Sullivan |
| 2013/0253700 A1 | 9/2013 | Carson et al. |
| 2013/0275314 A1 | 10/2013 | Bowles |
| 2013/0284805 A1 | 10/2013 | Kraft et al. |
| 2013/0290146 A1 | 10/2013 | West et al. |
| 2013/0297388 A1 | 11/2013 | Kyle, Jr. et al. |
| 2014/0012643 A1 | 1/2014 | Behrisch |
| 2014/0038556 A1 | 2/2014 | De Sousa |
| 2014/0067710 A1 | 3/2014 | Gventer et al. |
| 2014/0143161 A1 | 5/2014 | Ahn |
| 2014/0150100 A1 | 5/2014 | Gupta et al. |
| 2014/0156883 A1 | 6/2014 | Bowles |
| 2014/0214505 A1 | 7/2014 | Shuster-Arechiga et al. |
| 2014/0244315 A1 | 8/2014 | Cahill et al. |
| 2014/0347473 A1 | 11/2014 | Wolff et al. |
| 2015/0006281 A1 | 1/2015 | Takahashi |
| 2015/0066677 A1 | 3/2015 | Bowles et al. |
| 2015/0120485 A1 | 4/2015 | Nash |
| 2015/0193797 A1 | 7/2015 | Gerrity |
| 2015/0278529 A1 | 10/2015 | Cho et al. |
| 2016/0019685 A1 | 1/2016 | Nguyen |
| 2016/0055392 A1 | 2/2016 | Nakano |
| 2016/0091549 A1 | 3/2016 | Snook et al. |
| 2016/0092849 A1 | 3/2016 | Cirannek et al. |
| 2016/0098688 A1 | 4/2016 | Hunt et al. |
| 2016/0098689 A1 | 4/2016 | Bowles et al. |
| 2016/0098690 A1 | 4/2016 | Silva et al. |
| 2016/0125367 A1 | 5/2016 | Bowles et al. |
| 2016/0125548 A1 | 5/2016 | Bowles et al. |
| 2016/0125612 A1* | 5/2016 | Seki ................. G06T 3/0018 382/106 |
| 2016/0132840 A1 | 5/2016 | Bowles et al. |
| 2016/0171544 A1 | 6/2016 | Heminger et al. |
| 2016/0171575 A1 | 6/2016 | Bowles et al. |
| 2016/0210648 A1 | 7/2016 | Cirannek |
| 2016/0269401 A1 | 9/2016 | Saito et al. |
| 2016/0275460 A1 | 9/2016 | Ploetner et al. |
| 2016/0275518 A1 | 9/2016 | Bowles et al. |
| 2017/0083886 A1 | 3/2017 | Silva et al. |
| 2017/0091823 A1 | 3/2017 | Adinarayan et al. |
| 2017/0169401 A1 | 6/2017 | Beane et al. |
| 2017/0278191 A1 | 9/2017 | Tassone et al. |

FOREIGN PATENT DOCUMENTS

| | | |
|---|---|---|
| CN | 1864088 A1 | 11/2006 |
| CN | 1957320 A1 | 5/2007 |
| CN | 200965706 A1 | 10/2007 |
| CN | 102246384 A1 | 11/2011 |
| CN | 202351953 A1 | 7/2012 |
| CN | 202394296 A1 | 8/2012 |
| CN | 102654927 A1 | 9/2012 |
| CN | 102812500 A1 | 12/2012 |
| CN | 102930642 A1 | 2/2013 |
| CN | 102976004 A1 | 3/2013 |
| CN | 103198562 A1 | 7/2013 |
| CN | 103226870 A1 | 7/2013 |
| CN | 203242065 A1 | 10/2013 |
| CN | 103440607 A1 | 12/2013 |
| CN | 103544772 A1 | 1/2014 |
| CN | 203408902 A1 | 1/2014 |
| CN | 103662541 A1 | 3/2014 |
| CN | 103679147 A1 | 3/2014 |
| CN | 203520502 A1 | 4/2014 |
| CN | 203588366 A1 | 5/2014 |
| CN | 103954626 | 7/2014 |
| CN | 105513201 A1 | 4/2016 |
| EP | 1168253 A1 | 1/2002 |
| EP | 1703436 A1 | 9/2006 |
| GB | 2167553 | 5/1986 |
| JP | 07112801 A1 | 5/1995 |
| JP | 7334583 A1 | 12/1995 |
| JP | 2000121564 A2 | 4/2000 |
| JP | 3123095 | 1/2001 |
| JP | 2002019147 A1 | 1/2002 |
| JP | 2002183286 A1 | 6/2002 |
| JP | 2002259528 A1 | 9/2002 |
| JP | 2002302252 A1 | 10/2002 |
| JP | 2002324264 A1 | 11/2002 |
| JP | 2002358354 A1 | 12/2002 |
| JP | 2003139516 A1 | 5/2003 |
| JP | 2003242243 A1 | 8/2003 |
| JP | 2003264007 A1 | 9/2003 |
| JP | 2003267509 A1 | 9/2003 |
| JP | 2004021569 A1 | 1/2004 |

(56) References Cited

FOREIGN PATENT DOCUMENTS

| | | | |
|---|---|---|---|
| JP | 2004288143 A1 | 10/2004 |
| JP | 2004303102 A1 | 10/2004 |
| JP | 2004341681 A1 | 12/2004 |
| JP | 2006127308 A1 | 5/2006 |
| JP | 2006195814 A1 | 7/2006 |
| JP | 2006227764 A1 | 8/2006 |
| JP | 2006260246 A1 | 9/2006 |
| JP | 2007141266 A1 | 6/2007 |
| JP | 2007179516 A1 | 7/2007 |
| JP | 2007265340 A1 | 10/2007 |
| JP | 2008522299 A1 | 6/2008 |
| JP | 2008293391 A1 | 12/2008 |
| JP | 2007086725 A1 | 4/2009 |
| JP | 2009245058 A1 | 10/2009 |
| JP | 2009250971 A1 | 10/2009 |
| JP | 2010177720 A1 | 8/2010 |
| JP | 2012058932 A1 | 3/2012 |
| JP | 2013033361 A1 | 2/2013 |
| JP | 2013037441 A1 | 2/2013 |
| JP | 2013551823 A1 | 8/2013 |
| KR | 20000064168 A1 | 11/2000 |
| KR | 20130085255 A1 | 7/2013 |
| KR | 20140037543 A1 | 3/2014 |
| WO | 115096 A1 | 3/2001 |
| WO | 205176 A1 | 1/2002 |
| WO | WO-225613 | 3/2002 |
| WO | 239357 A1 | 5/2002 |
| WO | 3012717 A1 | 2/2003 |
| WO | 3014994 A1 | 2/2003 |
| WO | 2004021114 A1 | 3/2004 |
| WO | 2004114490 A1 | 12/2004 |
| WO | 2005008566 A1 | 1/2005 |
| WO | 2005101346 A1 | 10/2005 |
| WO | 2006058601 A1 | 6/2006 |
| WO | 2006080851 A1 | 8/2006 |
| WO | WO-2007066166 | 6/2007 |
| WO | 9128176 A1 | 10/2009 |
| WO | 2009128173 A1 | 10/2009 |
| WO | 2009129526 A1 | 10/2009 |
| WO | 2010040116 A1 | 4/2010 |
| WO | 2010128267 A1 | 11/2010 |
| WO | 2010128315 A1 | 11/2010 |
| WO | 2011131016 A1 | 10/2011 |
| WO | 2012138679 A1 | 10/2012 |
| WO | 2013074819 A1 | 5/2013 |
| WO | WO-2013/063042 A1 | 5/2013 |
| WO | WO-2014075055 | 5/2014 |
| WO | 2015022409 A1 | 2/2015 |

OTHER PUBLICATIONS

Kanter, James Max, "Color Crack:Identifying Cracks in Glass," dated Dec. 9, 2014; retrieved from the internet http://www.jmaxkanter.com/static/papers/color_crack.pdf on Sep. 22, 2017.

Oliveira, et al., "Automatic crack detection on road imagery using anisotropic diffusion and region linkage," 18th European Signal Processing Conference (EUSIPCO-2010), Aug. 23, 2010, pp. 274-278.

Zhang, Yiyang, "The design of glass crack detection system based on image preprocessing technology," 2014 IEEE 7th Joint International Information Technology and Artificial Intelligence Conference, IEEE, Dec. 20, 2014; pp. 39-42.

2006 Florida Statutes Title XXXIII, Chapter 538, Sections 538.03 and 538.04, 7 pages.

Aftermarket Cellular Accessories, "Cellular Phone Model Identification," retrieved from http://web/archive.org/web/20060328064957/http://aftermarketcellular.com/ic/identification.html on Mar. 16, 2014, published Mar. 28, 2006, 3 pages.

Altec Lansing User's Guide 2007, 8 pages.

Bussiness Wire, "The World's First Office Photography Machine" at CES 2008 Launched by Ortery Technologies, Jan. 7, 2008, 3 pages.

CNET, "Tackling LCD "burn ins", and dead/stick Pixels", published Sep. 2, 2009, retrieved from http://www.cnet.com/news/tackling-lcd-burn-ins-and-deadstuck-pixels/.

Evgenii Masunov, Mar. 25, 2010, http://www.appleinsider.ru/news/ipone-obladaet-luchshim-tachskrinom-provereno_robotom.html, 4 pages.

Geekanoids, You Tube Video, "Apple iPhone 3GS Unboxing and Review", uploaded on Jun. 19, 2009, retrieved from http://www.youtube.com/watch?v=GCEi9QAeDqk on Sep. 2, 2009.

GSM Arena Glossary, "LCD (Liquid Crystal Display", retrieved from http://www.gsmarena.com/glossary.php3?term=lcd on Apr. 28, 2016, 1 page.

Lambert, Emily, "Use It Up, Wear It Out", Forbes 175.5 (2005): 77-78. Business Source Complete. Web. Jan. 6, 2015, 3 pages.

Littleton Partners with Donations Ink (Jan. 19, 2006) US Fed News Service, Including US State News. Web. Jan. 6, 2015, 1 page.

MobileGazette.com, "2006 in Review: The Good, The Bad and the Ugly", published Dec. 2006, retrieved from http://www.mobilegazette.com/2006-review-06x12x22.htm on Nov. 11, 2015.

PC World, "Wipe Your Cell Phone's Memory Before Giving it Away", published Jan. 2006, retrieved from http://www.washingtonpost.com/wp-dyn/content/article/2006/01/30/AR2006013001144.html on Nov. 10, 2015.

Perng et al., "A Novel Vision System for CRT Panel Auto-Inspection", Proceedings of the 2005 IEEE International Conference on Mechatronics, Jul. 10-12, 2005, pp. 4.

Perng et al., "A Novel Vision System for CRT PaNnel Auto-Inspection", Journal of the Chinese Institute of Industrial Engineers, vol. 24, No. 5, pp. 341-350 (2007).

Rawson, Chris, "TUAW: 25 Ways to Check the Hardware on Your iPhone 4", published Aug. 12, 2010, retrieved at http://www.tuaw.com/2010/08/13/hardware-test-your-iphone-4/ on Feb. 28, 2014.

Rehg et al. "Vision for a Smart Kiosk" IEEE, Computer Society Conference on Computer Vision and Pattern Recognition (1997).

Rolf Steinhilper "Remanufacturing: The Ultimate Form of Recycling", Fraunhofer IRBVerlag, 1998, parts 1-3, http://www.reman.org/Publications_main.htm.

SimplySellular, "Get Cash for your Old Cell Phone", published Apr. 2, 2010, retrieved from http://simplysellular.com/conditions.php on Jan. 6, 2015, 2 pages.

Wilson, Doug, "Liquid Crystal Display (LCD) Inspection System", National Instruments Case Study, available May 10, 2009, retrieved from http://sine.ni.com/cs/app/cod/p/id/cs-345 on Jan. 5, 2015, 2 pages.

Yahoo Answers, "What is a Clean ESN?" published Jun. 23, 2009, retrieved from http://web.archive.org/web/20090623215042/http://answers.yahoo.com/question/inde,8020US?qid=20080318061012AANFRco on Apr. 3, 2014.

Co-Pending U.S. Appl. No. 15/130,851 of Forutanpour, B. et al., filed Apr. 15, 2016.

Co-Pending U.S. Appl. No. 15/630,508 of Silva, J. et al., filed Jun. 22, 2017.

Co-Pending U.S. Appl. No. 15/630,539 of Bowles, M. et al., filed Jun. 22, 2017.

Investopedia: What's the difference between weighted average accounting and FIFO/LILO accounting methods? Aug. 19, 2010. Accessed via archive.org [https://web.archive.org/web/20100819200402/http://www.investopedia.com/ask/answers/09/weighted-average-fifo-lilo-accounting.asp].

Dennis Bournique: "Mobile Karma Shuts Down As iCloud and Blacklists Challenge Used Phone Buyers", Prepaid Phone News, Jul. 23, 2014 (Jul. 23, 2014), XP055229747, Retrieved from the Internet <URL:http://www.prepaidphonenews.com/2014/07/mobile-karma-shuts-down-as-icloud-and.html>; accessed Nov. 27, 2017; 2 pages.

Tecace Software: "Your phone appraisal—Movaluate—Android Apps on Google Play", Android Apps on Google Play, Aug. 12, 2013 (Aug. 12, 2013), XP055230264, Retrieved from the Internet <URL:https://play.google.com/store/apps/details?id=com.tecace.android.app.movaluate&hl=en>; accessed Nov. 27, 2017; 2 pages.

Co-Pending U.S. Appl. No. 15/855,320 of Forutanpour et al., filed Dec. 27, 2017.

* cited by examiner

METHODS AND SYSTEMS FOR DETECTING CRACKS IN ELECTRONIC DEVICES

TECHNICAL FIELD

The present disclosure is directed generally to methods and systems for evaluating mobile phones and other consumer electronic devices and, more particularly, to methods and systems associated with detecting cracks in screens of such devices.

BACKGROUND

It is often necessary to visually evaluate a screen of a mobile device (e.g., a smartphone or tablet) to identify cracks or other defects in the mobile device. For example, pricing the mobile device, assessing the mobile device for possible repair, and evaluating the mobile device for warranty coverage all may require identification of any cracks in the mobile device's screen and/or in non-screen portions of the device. Individualized manual inspection of mobile device screens for cracks is slow, cumbersome, and can yield inconsistent results. Current automated methods for detecting cracks in other contexts are often over-inclusive resulting in high rates of false-positive crack indications. Accordingly, there is a need for improved methods and systems for automatically detecting cracks in mobile device screens.

DETAILED DESCRIPTION

Overview

Figure 1:
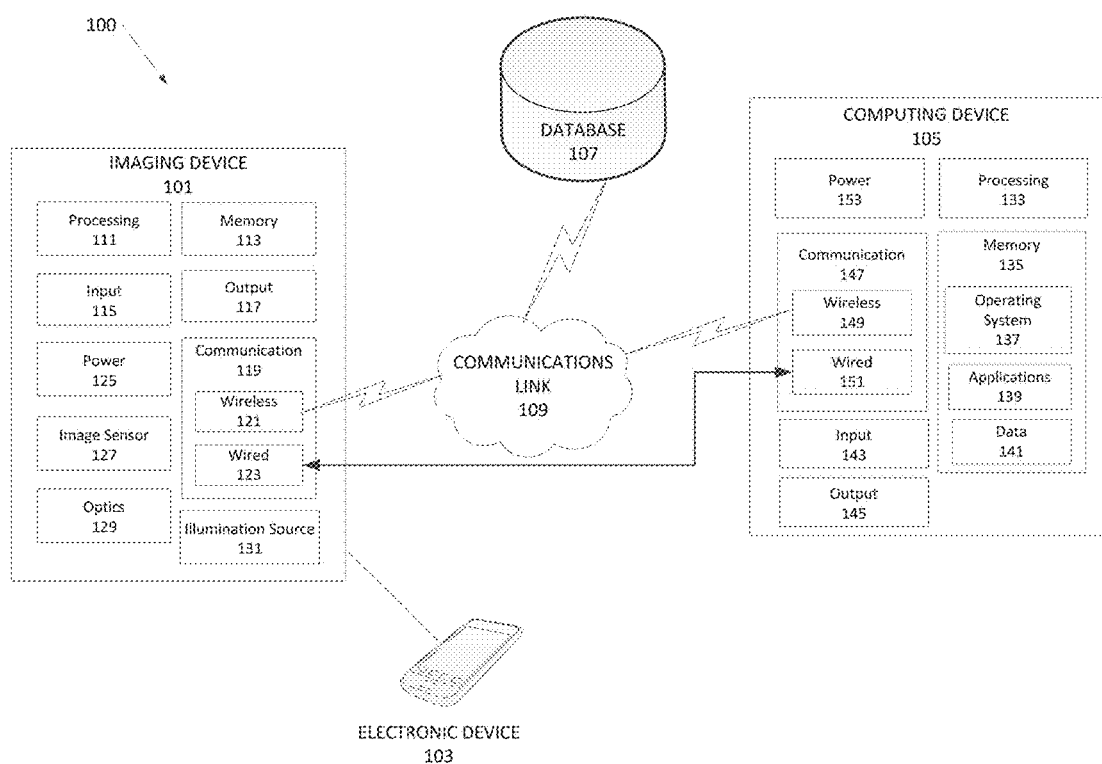
FIG. 1 is a block diagram illustrating components of a suitable computing environment for implementing various aspects of the present technology.

The following disclosure describes systems and methods for automated visual inspection and evaluation of electronic device screens. In particular, at least some embodiments of the present technology enable automatic crack detection in electronic device screens. In one embodiment, an image of an electronic device screen is automatically analyzed to detect cracks therein. First, edges can be automatically identified in the image (e.g., using a Canny edge detector or another edge-detection algorithm). Next, close proximity edge pairings can be identified. For example, for each identified edge, the routine can determine whether a corresponding adjacent edge is present within a predetermined distance. With this approach, edges with nearby adjacent edges can be identified. Such edge-nonedge-edge groupings, or edge pairings, are indicative of a genuine crack rather than an artifact such as a reflection or fingerprint. Further processing can be performed, for example assigning various weights to the identified edges, identifying straight line segments from the identified edges (e.g., using a Hough line transform or another straight-line detector), etc. Based on these analyses, a crack detection score can be calculated.

Certain details are set forth in the following description and in FIGS. 1-5D to provide a thorough understanding of various embodiments of the present technology. In other instances, well-known structures, materials, operations and/or systems often associated with smartphones and other handheld devices, consumer electronic devices, computer hardware, software, and network systems, etc. are not shown or described in detail in the following disclosure to avoid unnecessarily obscuring the description of the various embodiments of the technology. Those of ordinary skill in the art will recognize, however, that the present technology can be practiced without one or more of the details set forth herein, or with other structures, methods, components, and so forth. The terminology used below should be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be specifically defined as such in this Detailed Description section.

The accompanying Figures depict embodiments of the present technology and are not intended to be limiting of the scope of the present technology. The sizes of various depicted elements are not necessarily drawn to scale, and these various elements may be arbitrarily enlarged to improve legibility. Component details may be abstracted in the Figures to exclude details such as the position of components and certain precise connections between such components when such details are unnecessary for a complete understanding of how to make and use the invention.

In the Figures, identical reference numbers may identify identical, or at least generally similar, elements. To facilitate the discussion of any particular element, the most significant digit or digits of any reference number may refer to the Figure in which that element is first introduced. For example, element 110 is first introduced and discussed with reference to FIG. 1.

Crack Detection in Electronic Devices

FIG. 1 illustrates an embodiment of an environment 100 in which various aspects of the present technology can be implemented. The environment 100 includes an imaging device 101 configured to obtain images and/or video of an electronic device 103 (e.g., a mobile phone, tablet, notebook, etc.). The imaging device 101 is in communication with a computing device 105 and a database 107 via a communications link 109.

The imaging device 101 includes a processing component 111, a memory 113, input and output components 115 and 117, and a power component 125. The imaging device 101 further includes an image sensor 127, associated optics 129 and an illumination source 131. A communication component 119 of the imaging device 101 includes a wired connection 123 and a wireless transceiver 121. The computing device 105 can include several components similar to components of the imaging device 101. For example, the computing device 105 can include a processing component 133, memory 135 (which can store an operating system 137, applications 139, and data 141), along with input 143 and output 145 components and a power component 153. A communication component 147 of the computing device 105 includes a wired connection 151 and a wireless transceiver 147. These features of the imaging device 101 and the computing device 105 are described in more detail below in the context of a routine for detecting cracks in device screens in accordance with an embodiment of the present technology.

Figure 2A:
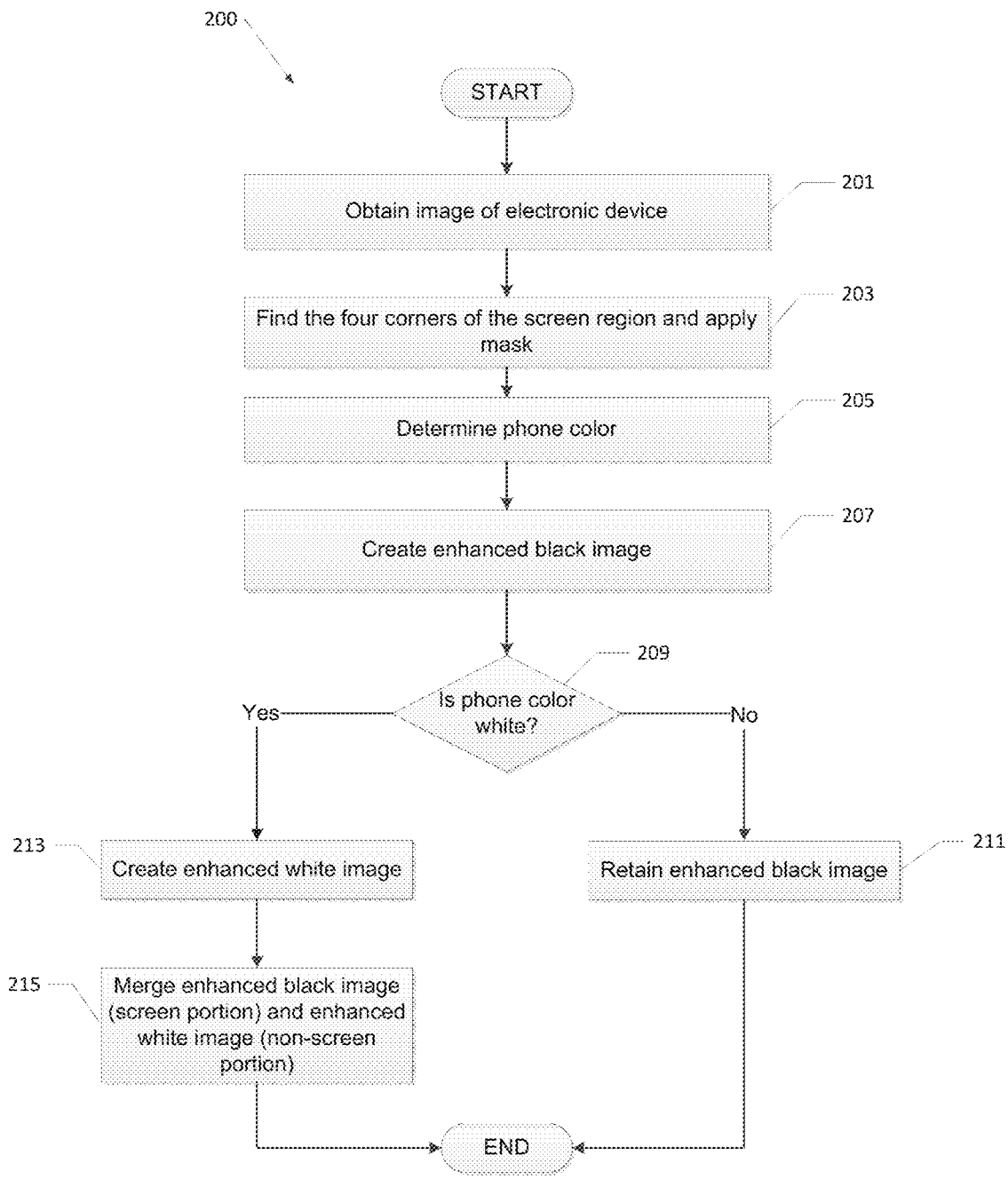
FIG. 2A is a flow diagram of a routine for enhancing images of electronic devices in accordance with an embodiment of the present technology.

FIG. 2A is a flow diagram of a routine 200 for enhancing an image of an electronic device in accordance with an embodiment of the present technology. Creating enhanced images can aid in the crack detection process. The process for creating such enhanced images can vary depending on the color of the electronic device. In some embodiments, the routine 200 can be performed by the computing device 105, which is described in more detail below. In block 201, the routine 200 obtains an image of the electronic device 103. For example, the imaging device 101 can be used to obtain one or more images of the electronic device 103. In some embodiments, the images are included in a video of the electronic device 103. For example, the imaging device 101 can be moved relative to the electronic device 103 or vice versa to obtain different views of the electronic device 103 on the video. A similar approach can be taken using still images, such as by taking a number of still images with the imaging device 101 at different orientations relative to the electronic device 103. For example, the imaging device 101 and/or the electronic device 103 can be affixed to moveable components such as a moveable platform or mounting surface. The moveable components can be controlled and moved using a belt drive, rack and pinion system, or other suitable drive system coupled to an electronic controller (e.g., the computing device 105). Furthermore, the routine 200 can obtain various images of the electronic device 103 under different conditions, for example under different lighting conditions (e.g., no lights on, all lights on, only infrared illumination, etc.), under different operating conditions (e.g., with a display of the electronic device 103 in an "off" mode, with the display in an "on" mode, with the display presenting a predetermined image (e.g. a QR code or other known image), etc.). In other embodiments, the routine 200 can obtain a single image of the electronic device 103 and/or images the electronic device 103 under a single operating condition. With reference again to the routine 200, the image or images obtained by the imaging device 101 can be transmitted to the computing device 105, such as via the communications link 109, for analysis and evaluation.

In block 203, the routine 200 finds the four corners of the screen region and applies a mask to the image. For example, the mask can separate the image into a screen region and a non-screen region. In some embodiments, the screen region can be dilated with respect to the actually identified four corners of the screen so as to include at least a portion of the area outside of the device screen. The corners of the screen region can be identified using edge detection or other suitable techniques.

In block 205, the routine 200 determines the phone color. For example, the routine 200 can evaluate the average brightness of pixels in the non-screen region of the phone to determine if they exceed a predetermined threshold. Higher average brightness in this region can indicate a white phone, while lower average brightness can indicate a black phone. Other suitable approaches can be used to determine the phone color, for example calculating a color histogram of the non-screen portion of the phone or other such technique.

In block 207, the routine 200 creates an "enhanced black image" in which the image is modified so as to render cracks more visible in black phones or in the screen portion of white phones (which are generally black). This enhanced black image can be created, for example, by calculating the average brightness of the screen portion and determining how much that average brightness must be multiplied by to get some set value (e.g., 140 brightness values). That multiplier factor can be clipped to some maximum, for example 6.3. Other set values of brightness values and maximum multiplier factors can be used. The entire image can then be multiplied by this determined multiplier factor such that both the screen region portion and the non-screen portion have increased brightness levels.

In block 209, the routine 200 determines whether the phone color is white. If not, then the routine 200 continues to block 211 and retains the black enhanced image generated in block 207. This enhanced black image can be used to detect cracks in black phones, as the enhancement applied to both the screen portion and non-screen portion can aid in detecting cracks in those regions. Although this description refers to "white" and "black" devices, the routine can be equally applied to a variety of dark-colored and light-colored devices, and the devices need not be substantially white or substantially black.

If, in block 209, the phone color is white, then the routine 200 continues to block 213 to create an "enhanced white image." This enhanced white image can be generated by computing a histogram of the entire image and setting all pixels less than some shadow cutoff (e.g., approximately 100 brightness values, or the 25th percentile of brightness in the image). In some embodiments, the shadow cutoff can be approximately 100 brightness values. Next, the routine 200 can set all pixels greater than some highlight cutoff (e.g., approximately 185 brightness values, or the 75th percentile of brightness in the image) to the maximum brightness value of 255. The routine 200 can then stretch all remaining values between the shadow cutoff and the highlight cutoff (e.g., between 100 and 185, or between the 25th and 75th percentiles of brightness in the image) to a range between 0 and 255 brightness values. This produces an enhanced white image in which cracks in the non-screen portions of white phones are more easily visible.

In block 215, the routine 200 merges the enhanced black image and the enhanced white image. For example, the routine 200 can retain the screen portion of the enhanced black image (as the screen portion of the white phone is generally black) and retain the non-screen portion of the enhanced white image (since this non-screen portion of the white phone is white). This merged image includes high visibility of cracks in the screen (black) portion of the image as well as high visibility of cracks in the non-screen (white) portion of the image. After block 215, the routine ends.

Figure 2B:
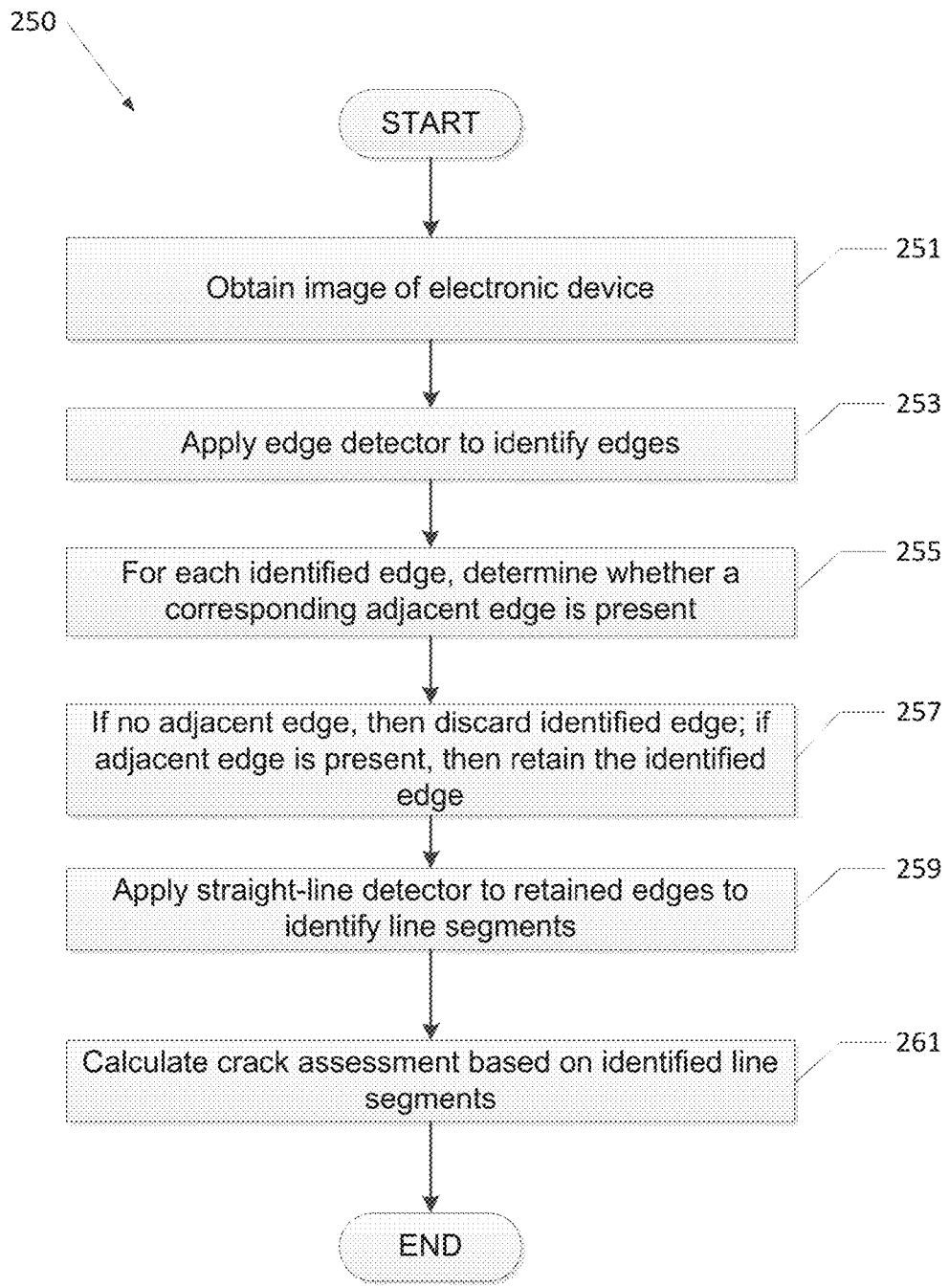
FIG. 2B is a flow diagram of a routine for detecting cracks in device screens in accordance with an embodiment of the present technology.

FIG. 2B is a flow diagram of a routine 250 for detecting cracks in device screens in accordance with an embodiment of the present technology. In some embodiments, the routine 250 can be performed by the computing device 105, which is described in more detail below. In block 251, the routine 250 obtains an image of the electronic device 103. For example, the imaging device 101 can be used to obtain one or more images of the electronic device 103. In some embodiments, the image can be an enhanced image as produced by the routine 200 described above with respect to FIG. 2A.

In block 253, the routine 250 applies an edge detector (e.g., a Canny edge detector) to the image to identify edges. In a particular example, the edge detector identifies points in the image at which the image brightness changes sharply or has discontinuities. The identified points can then be organized into a set of line segments termed "edges." A Gaussian or other suitable filter can then be applied to smooth the image and reduce noise. The edge detector can identify intensity gradients in the image. A non-maximum suppression can be applied to eliminate spurious response to edge detection. A threshold (e.g., a double threshold) can then be applied to determine potential edges. Finally, a hysteresis approach can be used to suppress potential edges that are weak and/or not connected to strong edges.

The routine 250 can perform any number of pre-processing steps prior to and/or after applying the edge detector to the image. For example, the image can be enhanced, inverted, cropped, dilated, merged with other images (e.g., merging a high contrast image with a low contrast image), etc.

Although a Canny edge detector is described above, various other edge detection algorithms can be used in its place. For example, the routine can include applying other gradient operator methods such as Extended Prewitt 7×7 and Abdou, thresholding and linking, edge thinning, differential edge detection, phase congruency-based edge detection, etc.

In block 255, the routine 250 determines, for each identified edge, whether a corresponding adjacent edge is present. For example, for each identified edge, the routine can determine whether another identified edge is located within a predetermined distance (e.g., within 10 pixels, within 9, 8, 7, 6, 5, 4, 3, 2, or 1 pixel, etc.). In some embodiments, the predetermined distance can be determined as a number of pixels that correspond to a predetermined physical distance, for example given a resolution and imaging distance such that 7 pixels correspond to approximately 1 millimeter in physical distance on the device, the predetermined distance can be 10 pixels in one example, which correspond to a physical distance of approximately 1.3 mm. In various embodiments, the predetermined distance can correspond to a range of physical distances, e.g., within 2 mm, within 1.5 mm, within 1 mm, within 0.5 mm, etc. In some embodiments, the routine 250 determines, at each point along an identified edge, whether another identified edge falls within the predetermined distance by analyzing the spacing along two or more axes. For example, for a given pixel that has been found to be on one of the identified edges, the routine 250 can determine whether the next pixel to the right is also on an identified edge. If not, but the next pixel to the right (i.e., two pixels to the right of the original pixel) does fall along an identified edge, then the original pixel can be retained. This procedure can be repeated in several directions (e.g., up, down, left, and right), and at a pre-selected proximity threshold (e.g., determining whether another edge is located within 5 pixels, within 7 pixels, etc.). With this approach, the routine 250 can identify edges associated with nearby edges. Such edge-nonedge-edge groupings, or edge pairings, are indicative of a genuine crack rather than an artifact such as a reflection or fingerprint. In block 257, the routine 250 discards those edges for which no adjacent edge was identified. Alternatively, the edges for which no adjacent edge was identified can be assigned a lower weight rather than being discarded entirely.

In the illustrated embodiment, the routine 250 next applies a straight-line detector (e.g., a suitable Hough transform) to the retained edges to identify line segments (block 259). For example, a Hough transform can be applied and varied based on three tuning parameters: (1) the minimum number of intersections to detect a line, (2) the minimum number of points that can form a line, and (3) the maximum gap between two points to be considered in the same line. These three parameters can be varied to maximize the number of cracks identified using such a Hough transform. In one example, the first parameter can have a value of between 10 and 20, e.g., approximately 15; the second parameter can have a value of between 15 and 20, e.g., approximately 18, and the third parameter can have a value between 5 and 15, e.g. approximately 10. Solely by way of theory, and without wishing to be limited to any particular theory, cracks in mobile device screens may tend to be straight or at least capable of being represented by a series of straight lines, whereas extraneous features (e.g., fingerprints and reflections) may be more likely to follow curved paths. In other embodiments, applying the straight-line detector is omitted. For example the routine 250 can further process all of the retained edges from block 257.

With reference again to FIG. 2B, the routine 250 next calculates a crack assessment score based on the identified line segments (block 261). In some embodiments, the crack assessment score is a percentage of total pixels that are included in the identified line segments from block 259. For example, if 3,000 pixels are included in the identified line segments out of a total of 727,040 pixels (of a 1136×640 pixel screen), then the crack assessment score can indicate that 0.413% of the screen is cracked. In other embodiments, the crack assessment score can assign a varying weight to each pixel depending on whether it falls along the identified line segments in block 259. For example pixels falling along the identified line segments can be assigned a higher weight than pixels falling outside of the identified line segments. In both cases, a higher assessment score can indicate a greater degree of cracking in the screen.

Figure 3A:
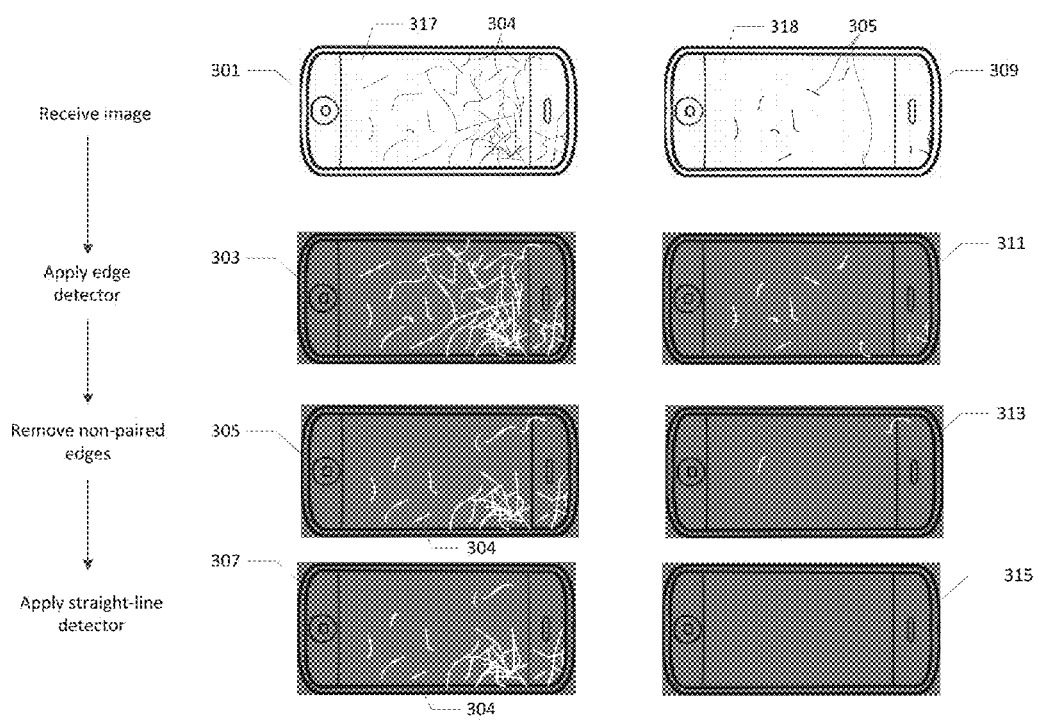
FIG. 3A is a flow diagram of selected operations in the method shown in FIG. 2B along with corresponding images of electronic devices.

FIG. 3A illustrates example images of mobile devices at various stages of the routine 250. As noted above, images of a mobile device are received for evaluation and assessment. Image 301 is an image of a mobile device 317 having a cracked screen 317 with a plurality of cracks 304. Image 309 is an image of a mobile device having a non-cracked screen 318 with a plurality of artifacts 305 (e.g., smudges, reflections, fingerprint marks, etc.). These images can be pre-processed after being received, for example by enhancing contrast, cropping, dilating, etc. As noted above with respect to block 253, an edge detector is applied to the images to identify edges. Image 303 is the output of the edge detector for the cracked mobile device, and image 311 is the output of the edge detector for the non-cracked mobile device. As seen in these images, cracks (e.g., cracks 304) are identified as edges, as are various other stray marks (e.g., artifacts 305) across the screens of the cracked and non-cracked devices. As noted above, in some embodiments the edge detector is applied to a portion of the input image as defined by a mask. In this way, known features (e.g., a screen border, a home button, etc.) may be excluded.

As described above with respect to blocks 255 and 257, the output of the edge detector can be further filtered by determining, for each edge, whether a corresponding adjacent edge is present within a predetermined distance. If no adjacent edge is found within the predetermined distance, then the edge is determined not to be a crack and is discarded, otherwise it is retained. Image 305 is the output of this step on the cracked mobile device and image 313 is the output of this step on the non-cracked mobile device. Image 305 shows a reduced number of edges compared to image 303. Similarly, image 313 shows a reduced number of edges compared to image 311. As illustrated, the cracks 304 have been identified and retained in image 305, indicating the presence of edge-nonedge-edge pairings. This step results in a more accurate assessment of the degree of crack damage in the screen, by removing, for example, edged features that are wider than the predetermined distance (e.g., wider than 10 pixels). These relatively wide features are less likely to be genuine cracks and more likely to be reflections, smudges, or other artifacts in the image.

Figure 3B:
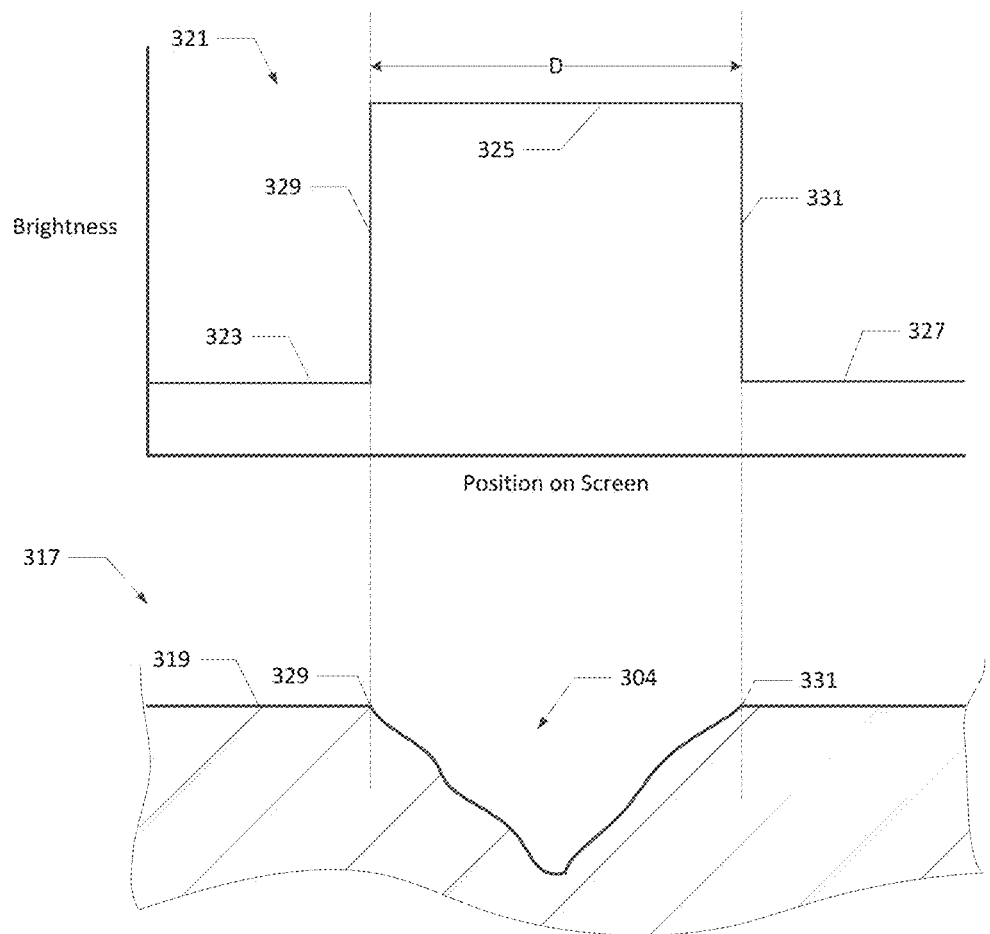
FIG. 3B is a cross-sectional view of a crack in an electronic device screen and a graph of corresponding brightness measured across the screen.

FIG. 3B illustrates an enlarged cross-sectional view of the crack 304 in a surface 319 of the electronic device screen 317. FIG. 3B also includes a graph 321 that illustrates the brightness in the image of this portion of the screen 317. A first portion 323 of the graph 321 indicates a relatively low level of brightness corresponding to a portion of the screen 317 to the left of a first edge 329 the crack 304. Similarly, a second portion 327 of the graph 321 indicates a relatively low level of brightness corresponding to a portion of the screen 317 to the right of a second edge 331 of the crack 304. The brightness level is significantly higher in a third portion 325 of the graph 321 in the area corresponding to the crack 304. This increased level of brightness in the third portion 325 corresponds to the first edge 329 between the first portion 323 and the third portion 325 of the graph 321, and the second edge 331 between the third portion 325 and the second portion 327 of the graph 321. The first edge 329 can be characterized as a "rising edge" indicating that the brightness rises from left to right while the second edge 331 can be characterized as a "falling edge" indicating that the brightness falls from left to right. Together, the first edge 329, the third portion 325, and the second edge 331 are an edge-nonedge-edge grouping, in which the first edge 329 and the second edge 331 are separated by a distance D. This distance D can be compared to the predetermined distance described above (e.g., within 10 pixels, within 9, 8, 7, 6, 5, 4, 3, 2, or 1 pixel, etc.). If the distance D is less than the predetermined distance (i.e., the first edge 329 and the second edge 331 are closer to one another than the predetermined distance), then the identified edges 329 and 331 are retained as indicative of a genuine crack. This procedure can be repeated in several directions (e.g., up, down, left, and right), and at a pre-selected proximity threshold (e.g., determining whether the distance D is less than 5 pixels, less than 7 pixels, etc.). With this approach, the routine can identify edges associated with nearby edges. If the distance D is found to be greater than the predetermined distance, then the edges 329 and 331 can be discarded if no other adjacent edges are found. Alternatively, the edges for which no adjacent edge was identified can be assigned a lower weight rather than being discarded entirely.

Although the illustration in FIG. 3B shows edges 329 and 331 corresponding geometrically to the outer positions of the physical crack 304 in the screen 317, this need not be the case in practice. Rather, various shapes and types of cracks can produce different variations in brightness having various edges. The routine 250 as described above can analyze the brightness to identify edge-nonedge-edge pairings to identify those edges that are more likely to correspond to genuine cracks in the screen.

Referring again to FIG. 3A, as described above with respect to block 259, a straight-line detector is then applied to the images. Image 307 is the result of the straight-line detector for the cracked device, and image 315 is the result of the straight-line detector for the non-cracked device. The straight-line detector can be configured to set all pixels that are part of identified lines to be white, as illustrated in image 307. The crack assessment score can then be determined by calculating the number white pixels as a proportion of the total screen or device pixels. As shown in image 315, the two filters removed essentially all of the non-crack edges present in the image 309. Accordingly, the non-cracked mobile device shown in images 309-315, which would otherwise have been falsely identified as cracked, can be accurately identified as non-cracked.

Computing Environment

Referring again to FIG. 1, additional details are set forth below regarding the computing environment in which the routine 250 can be performed. The imaging device 101 can be, for example, a digital camera (e.g., having a CCD or CMOS sensor) capable of capturing still and/or moving images of the electronic device 103, and transmitting the captured images over the communications link 109 to remote devices. In some embodiments, the imaging device 101 includes a camera and an associated fixture, base, or other imaging area in which the electronic device 103 is to be placed for imaging. This can provide a standard background against which the images and/or video of the electronic device 103 are obtained. The imaging device 101 can be configured to move the camera and/or the associated optics in order to capture images and/or video of the electronic device 103 from various angles. The imaging device 101 can also include an illumination source (e.g., LEDs, fluorescent bulbs, lamps, etc.) which can also aid in obtaining images of the electronic device 103 under uniform lighting conditions.

The electronic device 103 can be, for example, a smartphone, a tablet, a laptop, a handheld gaming device, a media player, or any such device that has a screen or other surface that may suffer cracks or similar defects. Although many embodiments of the present technology are described herein in the context of mobile phones, aspects of the present technology are not limited to mobile phones and generally apply to other consumer electronic devices. Such devices include, as non-limiting examples, all manner of mobile phones; smartphones; handheld devices; personal digital assistants (PDAs); MP3 or other digital music players; tablet, notebook, ultrabook and laptop computers; e-readers; all types of cameras; GPS devices; set-top boxes and other media players; VoIP phones; universal remote controls; wearable computers; and larger consumer electronic devices, such as desktop computers, TVs, projectors, DVRs, game consoles, etc.

The computing device 105 can be a desktop computer or another suitable device. The computing device 105 is configured to receive images of the electronic device 103 from the imaging device 101 and to automatically analyze the images to detect the presence of cracks or other defects. In some embodiments, the computing device 105 is remote from the imaging device 101 and can be in communication via the communications link 109. In other embodiments, the computing device 105 is connected to the imaging device 101 via a hardwire connection, or in certain embodiments the imaging device 101 and the computing device 105 are integrated into the same machine. The computing device 105 is also in communication with the database 107 which can store data used in automatically analyzing the images of the electronic device 103. The database 107 may also store the results of the automatic analysis of the images, other data about the electronic device 103, etc.

In the illustrated embodiment, various devices, including the imaging device 101 and the computing device 105, can exchange information with one another via the communication link 109. Although the communication link 109 can include a publicly available network (e.g., the Internet with a web interface), a private communication link, such as an intranet or other network can also be used. Moreover, in various embodiments the imaging device 101 is connected to a host computer (not shown) that facilitates the exchange of information between the imaging device 101, the computing device 105, remote computers, mobile devices, etc.

In the illustrated embodiment, the imaging device 101 includes the processing component 111 that controls operation of the imaging device 101 in accordance with computer-readable instructions stored in memory 113. The processing component 111 may include any logic processing unit, such as one or more central processing units (CPUs), graphics processing units (GPUs), digital signal processors (DSPs), application-specific integrated circuits (ASICs), etc. The processing component 111 may be a single processing unit or multiple processing units in an electronic device or distributed across multiple devices. Aspects of the present technology can be embodied in a special purpose computing device or data processor that is specifically programmed, configured, or constructed to perform one or more of the computer-executable instructions explained in detail herein. Aspects of the present technology can also be practiced in distributed computing environments in which functions or modules are performed by remote processing devices that are linked through a communications network, such as a local area network (LAN), wide area network (WAN), or the Internet. In a distributed computing environment, modules can be located in both local and remote memory storage devices.

The processing component 111 is connected to memory 113, which can include a combination of temporary and/or permanent storage, and both read-only memory (ROM) and writable memory (e.g., random access memory or RAM), writable non-volatile memory such as flash memory or other solid-state memory, hard drives, removable media, magnetically or optically readable discs, nanotechnology memory, biological memory, and so forth. As used herein, memory does not include a transitory propagating signal per se. The memory 213 includes data storage that contains programs, software, and information, such as an operating system and data. Imaging device 101 operating system and data can include software and databases configured to control imaging device 101 components, process images, communicate and exchange data and information with remote computers and other devices, etc.

The imaging device 101 further includes input components 115 that can receive input from user interactions and provide input to the processing component 111, typically mediated by a hardware controller that interprets the raw signals received from the input device and communicates the information to the processing component 111 using a known communication protocol. Examples of an input component 115 include touchpad, a keyboard (with physical or virtual keys), a pointing device (such as a mouse, dial, or eye tracking device), a touchscreen that detects contact events when it is touched by a user, a microphone that receives audio input, etc. The imaging device 101 can also include various other input components 115 such as GPS or other location determination sensors, motion sensors, wearable input devices with accelerometers (e.g. wearable glove-type input devices), biometric sensors (e.g., fingerprint sensors), light sensors, card readers (e.g., magnetic stripe readers or memory card readers) or the like.

The processing component 111 is also connected to one or more various output components 117, e.g., directly or via a hardware controller. The output devices can include a display on which text and graphics are displayed. The display can be, for example, an LCD, LED, or OLED display screen, an e-ink display, a projected display (such as a heads-up display device), and/or a display integrated with a touch-screen that serves as an input device as well as an output device that provides graphical and textual visual feedback to a user. The output components 117 can also include a speaker for playing audio signals, haptic feedback devices for tactile output such as vibration, etc. In some implementations, a speaker and microphone are implemented by a combined audio input-output device.

In the illustrated embodiment, the imaging device 101 further includes one or more communication components 119. The communication components can include, for example, a wireless transceiver 121 (e.g., one or more of a Wi-Fi transceiver; Bluetooth transceiver; near-field communication (NFC) device; wireless modem or cellular radio utilizing GSM, CDMA, 3G and/or 4G technologies; etc.) and/or a wired network connection 123 (e.g., one or more of an Ethernet port, cable modem, FireWire cable, Lightning connector, universal serial bus (USB) port, etc.). The communication components 119 are suitable for communication between the imaging device 101 and other local and/or remote devices, e.g., the computing device 105, directly via a wired or wireless peer-to-peer connection and/or indirectly via the communication link 109 (which can include the Internet, a public or private intranet, a local or extended Wi-Fi network, cell towers, the plain old telephone system (POTS), etc.). For example, the wireless transceiver 121 of the imaging device 101 can connect to a wireless transceiver 149 of the computing device via the wireless connection. The imaging device 101 further includes power 125, which can include battery power and/or facility power for operation of the various electrical components associated with the imaging device 101.

The imaging device 101 further includes the image sensor 127, optics 129, and illumination source 131. The image sensor 127 can be, for example, a CCD sensor, a CMOS sensor, or any other type of image sensor or array of sensors. The image sensor 127 can be aligned with optics 129, for example one or more lenses, filters, or other optical elements configured to orient and modulate incoming light before it reaches the image sensor 127. The illumination source 131 can be configured to direct illumination towards the field of view of the imaging device 101, and can be any type of light source, for example LEDs, fluorescent bulbs, etc. In some embodiments, the illumination source 131 includes multiple different types of light sources which can be individually activated, for example infrared, ultraviolet, broadband, etc.

The computing device 105 includes several components similar to those in the imaging device 101. In the illustrated embodiment, the computing device 105 includes a processing component 133 that controls operation of the computing device 105 in accordance with computer-readable instructions stored in memory 135. The processing component 133 may be any logic processing unit, such as one or more central processing units (CPUs), graphics processing units (GPUs), digital signal processors (DSPs), application-specific integrated circuits (ASICs), etc. The processing component 133 may be a single processing unit or multiple processing units in an electronic device or distributed across multiple devices. The processing component 133 is connected to memory 135, which includes data storage that contains programs, software, and information, such as an operating system 137, application programs 139, and data 141. The operating system 137 can include, for example, Windows®, Linux®, Android™, iOS®, and/or an embedded real-time operating system. The application programs 139 and data 141 can include software and databases configured to control computing device 105 components, process and evaluate images received from the imaging device 101, communicate and exchange data and information with remote computers and other devices, etc.

The computing device 105 can include input components 143, such as a keyboard (with physical or virtual keys), a pointing device (such as a mouse, joystick, dial, or eye tracking device), a touchscreen, a microphone, and a camera for still photograph and/or video capture. The computing device 105 can also include various other input components 143 such as GPS or other location determination sensors, motion sensors, wearable input devices with accelerometers (e.g. wearable glove-type input devices), biometric sensors (e.g., fingerprint sensors), light sensors, card readers (e.g., magnetic stripe readers or memory card readers) and the like.

The processing component 133 can also be connected to one or more various output components 145, e.g., directly or via a hardware controller. The output devices can include a display such as an LCD, LED, or OLED display screen (such as a desktop computer screen, handheld device screen, or television screen), an e-ink display, a projected display (such as a heads-up display device), and/or a display integrated with a touchscreen that serves as an input device as well as an output device that provides graphical and textual visual feedback to the user. The output devices can also include a speaker for playing audio signals, haptic feedback devices for tactile output such as vibration, etc.

In the illustrated embodiment, computing device 105 further includes one or more communication components 147. The communication components can include, for example, a wireless transceiver 149 (e.g., one or more of a Wi-Fi transceiver; Bluetooth transceiver; near-field communication (NFC) device; wireless modem or cellular radio utilizing GSM, CDMA, 3G and/or 4G technologies; etc.) and/or a wired network connector port 251 (e.g., one or more of an Ethernet port, cable modem, FireWire cable, Lightning connector, universal serial bus (USB) port, etc.). The communication components 147 are suitable for communication between the computing device 105 and other local and/or remote computing devices, e.g., the imaging device 101 a via a wired or wireless peer-to-peer connection and/or indirectly via the communication link 109. For example, the wireless transceiver 149 of the computing device 105 can connect to the wireless transceiver 121 of imaging device 101, and/or the wired connector port 151 of the computing device 105 can connect to the wired connector port 123 of the imaging device 101. The computing device 105 further includes power 153, which can include battery power and/or facility power for operation of the various electrical components associated with the computing device 105.

Unless described otherwise, the construction and operation of the various components shown in FIG. 1 are of conventional design. As a result, such components need not be described in further detail herein, as they will be readily understood by those skilled in the relevant art. In other embodiments, the computing device 105 and the imaging device 101 include other features that may be different from those described above. In still further embodiments, the computing device 105 and/or the imaging device 101 include more or fewer features similar to those described above.

Kiosk Environment

Figure 4:
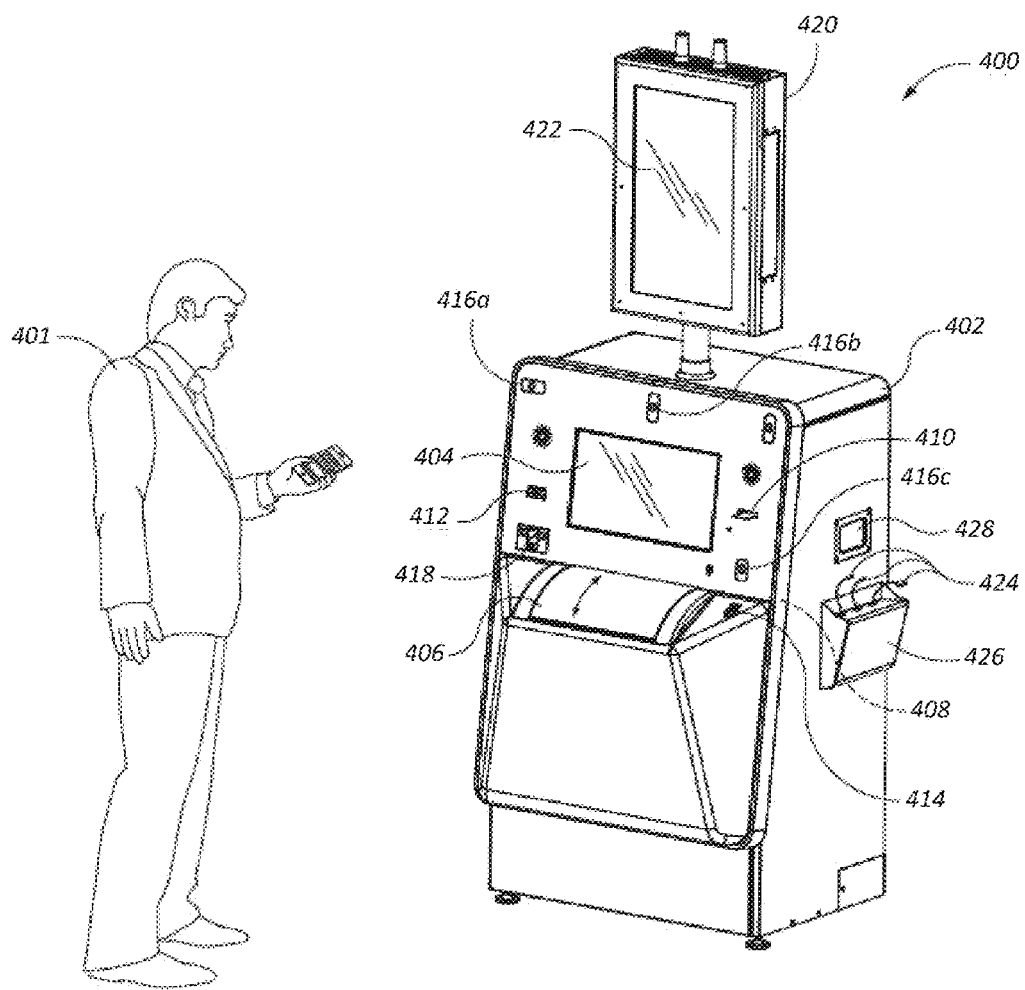
FIG. 4 is an isometric view of a machine employing methods and systems configured in accordance with embodiments of the present technology for recycling mobile phones and/or other electronic devices.

In some embodiments, the routines described herein can be carried out using a kiosk that includes an imaging device (e.g., the imaging device 101) therein. In some embodiments, the kiosk can perform some or all of the functions performed by the computing device 105 described above, for example processing and evaluating images received from the imaging device 101. The kiosk can include, for example, a processing component and memory storing instructions that, when executed by the processing component, perform operations such as the routine 250 described above. FIG. 4, for example, is an isometric view of a kiosk 400 for recycling and/or other processing of mobile phones and other consumer electronic devices in accordance with the present technology. The term "processing" is used herein for ease of reference to generally refer to all manner of services and operations that may be performed or facilitated by the kiosk 400 on, with, or otherwise in relation to an electronic device. Such services and operations can include, for example, selling, reselling, recycling, donating, exchanging, identifying, evaluating, pricing, auctioning, decommissioning, transferring data from or to, reconfiguring, refurbishing, etc., mobile phones and other electronic devices. Although many embodiments of the present technology are described herein in the context of mobile phones, aspects of the present technology are not limited to mobile phones and generally apply to other consumer electronic devices. Such devices include, as non-limiting examples, all manner of mobile phones, smart phones, handheld devices, PDAs, MP3 players, tablet, notebook and laptop computers, e-readers, cameras, etc. In some embodiments, it is contemplated that the kiosk 400 can facilitate selling and/or otherwise processing larger consumer electronic devices, such as desktop computers, TVs, game consoles, etc., as well smaller electronic devices such as Google Glass™, smart-watches, etc.

In the illustrated embodiment, the kiosk 400 is a floor-standing self-service kiosk configured for use by a user 401 (e.g., a consumer, customer, etc.) to recycle, sell, and/or perform other operations with a mobile phone or other consumer electronic device. In other embodiments, the kiosk 400 can be configured for use on a countertop or a similar raised surface. Although the kiosk 400 is configured for use by consumers, in various embodiments the kiosk 400 and/or various portions thereof can also be used by other operators, such as a retail clerk or kiosk assistant to facilitate the selling or other processing of mobile phones and other electronic devices.

In the illustrated embodiment, the kiosk 400 includes a housing 402 that is approximately the size of a conventional vending machine. The housing 402 can be of conventional manufacture from, for example, sheet metal, plastic panels, etc. A plurality of user interface devices are provided on a front portion of the housing 402 for providing instructions and other information to users, and/or for receiving user inputs and other information from users. For example, the kiosk 400 can include a display screen 404 (e.g., a liquid crystal display ("LCD") or light emitting diode ("LED") display screen, a projected display (such as a heads-up display or a head-mounted device), and so on) for providing information, prompts, etc., to users. The display screen 404 can include a touch screen for receiving user input and responses to displayed prompts. In addition or alternatively, the kiosk 400 can include a separate keyboard or keypad for this purpose. The kiosk 400 can also include an ID reader or scanner 412 (e.g., a driver's license scanner), a fingerprint reader 414, and one or more cameras 416 (e.g., digital still and/or video cameras, identified individually as cameras 416a-c). The kiosk 400 can additionally include output devices such as a label printer having an outlet 410, and a cash dispenser having an outlet 418. Although not identified in FIG. 4, the kiosk 400 can further include a speaker and/or a headphone jack for audibly communicating information to users, one or more lights for visually communicating signals or other information to users, a handset or microphone for receiving verbal input from the user, a card reader (e.g., a credit/debit card reader, loyalty card reader, etc.), a receipt or voucher printer and dispenser, as well as other user input and output devices. The input devices can include a touchpad, pointing device such as a mouse, joystick, pen, game pad, motion sensor, scanner, eye direction monitoring system, etc. Additionally the kiosk 400 can also include a bar code reader, QR code reader, bag/package dispenser, a digital signature pad, etc. In the illustrated embodiment, the kiosk 400 additionally includes a header 420 having a display screen 422 for displaying marketing advertisements and/or other video or graphical information to attract users to the kiosk. In addition to the user interface devices described above, the front portion of the housing 402 also includes an access panel or door 406 located directly beneath the display screen 404. As described in greater detail below, the access door is configured to automatically retract so that the user 401 can place an electronic device (e.g., a mobile phone) in an inspection area 408 for automatic inspection by the kiosk 400.

A sidewall portion of the housing 402 can include a number of conveniences to help users recycle or otherwise process their mobile phones. For example, in the illustrated embodiment the kiosk 400 includes an accessory bin 428 that is configured to receive mobile device accessories that the user wishes to recycle or otherwise dispose of. Additionally, the kiosk 400 can provide a free charging station 426 with a plurality of electrical connectors 424 for charging a wide variety of mobile phones and other consumer electronic devices.

Figure 5A:
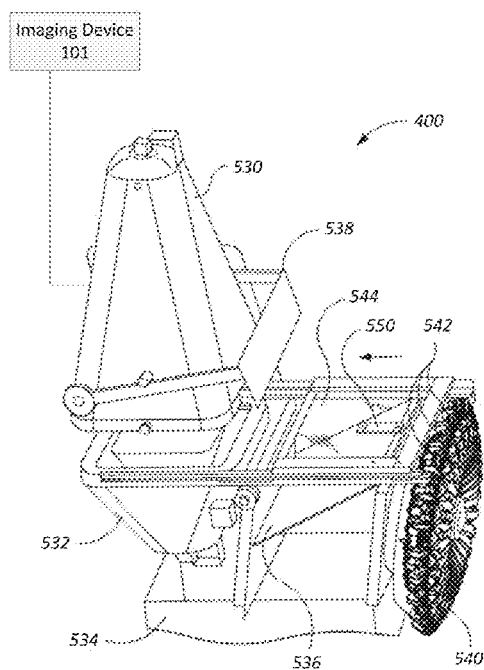
FIGS. 5A-5D are a series of isometric views of the machine of FIG. 4 with a number of exterior panels removed to illustrate operation of the machine in accordance with an embodiment of the present technology.

FIGS. 5A-5D are a series of isometric views of the kiosk 400 with the housing 402 removed to illustrate selected internal components configured in accordance with an embodiment of the present technology. Referring first to FIG. 5A, in the illustrated embodiment the kiosk 400 includes a connector carrier 540 and an inspection plate 544 operably disposed behind the access door 406 (FIG. 4). In the illustrated embodiment, the connector carrier 540 is a rotatable carrousel that is configured to rotate about a generally horizontal axis and carries a plurality of electrical connectors 542 (e.g., approximately 25 connectors) distributed around an outer periphery thereof. In other embodiments, other types of connector carrying devices (including both fixed and movable arrangements) can be used. In some embodiments, the connectors 542 includes a plurality of interchangeable USB connectors configured to provide power and/or exchange data with a variety of different mobile phones and/or other electronic devices. In operation, the connector carrier 540 is configured to automatically rotate about its axis to position an appropriate one of the connectors 542 adjacent to an electronic device, such as a mobile phone 550, that has been placed on the inspection plate 544 for recycling. The connector 542 can then be manually and/or automatically withdrawn from the connector carrier 540 and connected to a port on the mobile phone 550 for electrical analysis. Such analysis can include, e.g., an evaluation of the make, model, configuration, condition, etc.

In the illustrated embodiment, the inspection plate 544 is configured to translate back and forth (on, e.g., parallel mounting tracks) to move an electronic device, such as the mobile phone 550, between a first position directly behind the access door 406 and a second position between an upper chamber 530 and an opposing lower chamber 532. Moreover, in this embodiment the inspection plate 544 is transparent, or at least partially transparent (e.g., formed of glass, Plexiglas, etc.) to enable the mobile phone 550 to be photographed and/or otherwise optically evaluated from all, or at least most viewing angles (e.g., top, bottom, sides, etc.) using, e.g., one or more cameras, mirrors, etc. mounted to or otherwise associated with the upper and lower chambers 530 and 532. When the mobile phone 550 is in the second position, the upper chamber 530 can translate downwardly to generally enclose the mobile phone 550 between the upper chamber 530 and the lower chamber 532. The upper chamber 530 is operably coupled to a gate 538 that moves up and down in unison with the upper chamber 530.

In some embodiments, the kiosk 400 includes the imaging device 101 disposed within the upper hood 530. The imaging device 101 can be used as described above to facilitate visual inspection of the mobile phone 550 in order to detect cracks in the screen. The upper chamber 530 and/or the lower chamber 532 can also include one or more magnification tools, scanners (e.g., bar code scanners, infrared scanners, etc.) or other imaging components (not shown) and an arrangement of mirrors (also not shown) to view, photograph and/or otherwise visually evaluate the mobile phone 550 from multiple perspectives. In some embodiments, one or more of the cameras and/or other imaging components discussed above can be movable to facilitate device evaluation. For example, as noted above with respect to FIG. 1, the imaging device 101 can be affixed to a moveable mechanical component such as an arm, which in turn can be moved using a belt drive, rack and pinion system, or other suitable drive system coupled to an electronic controller (e.g., the computing device 105). The inspection area 408 can also include weight scales, heat detectors, UV readers/detectors, and the like, for further evaluation of electronic devices placed therein. The kiosk 400 can further include an angled binning plate 536 for directing electronic devices from the transparent plate 544 into a collection bin 534 positioned in a lower portion of the kiosk 400.

Figure 5B:
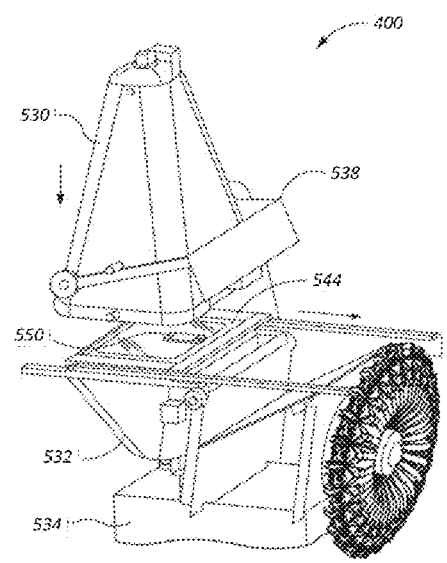

The kiosk 400 can be used in a number of different ways to efficiently facilitate the recycling, selling and/or other processing of mobile phones and other consumer electronic devices. Referring to FIGS. 4-5D together, in one embodiment a user wishing to sell a used mobile phone, such as the mobile phone 550, approaches the kiosk 400 and identifies the type of device the user wishes to sell in response to prompts on the display screen 404. Next, the user may be prompted to remove any cases, stickers, or other accessories from the device so that it can be accurately evaluated. Additionally, the kiosk 400 may print and dispense a unique identification label (e.g., a small adhesive-backed sticker with a quick response code ("QR code"), barcode, or other machine-readable indicia, etc.) from the label outlet 410 for the user to adhere to the back of the mobile phone 550. After this is done, the door 406 retracts and opens allowing the user to place the mobile phone 550 onto the transparent plate 544 in the inspection area 408 (FIG. 5A). The door 406 then closes and the transparent plate 544 moves the mobile phone 550 under the upper chamber 530 as shown in FIG. 5B. The upper chamber 530 then moves downwardly to generally enclose the mobile phone 550 between the upper and lower chambers 530 and 532, and the cameras and/or other imaging components in the upper and lower chambers 530 and 532 perform a visual inspection of the mobile phone 550. In one embodiment, the visual inspection of the mobile phone 550 includes performing the routines 200 (FIG. 2A) and/or 250 (FIG. 2B) to detect cracks in the screen. In some embodiments, the visual inspection includes a computer-implemented visual analysis (e.g., a three-dimensional ("3D") analysis) performed by a processing device within the kiosk (e.g., a CPU) to confirm the identification of the mobile phone 550 (e.g. make, model and/or sub-model) and/or to evaluate or assess the condition and/or function of the mobile phone 550 and/or its various components and systems. For example, the visual analysis can include computer-implemented evaluation (e.g., a digital comparison) of images of the mobile phone 550 taken from top, side and/or end view perspectives to determine length, width, and/or height (thickness) dimensions of the mobile phone 550. The visual analysis can further include a computer-implemented inspection of a display screen on the mobile phone 550 to check for, e.g., cracks in the glass and/or other damage or defects in the LCD (e.g., defective pixels, etc.).

Figure 5C:
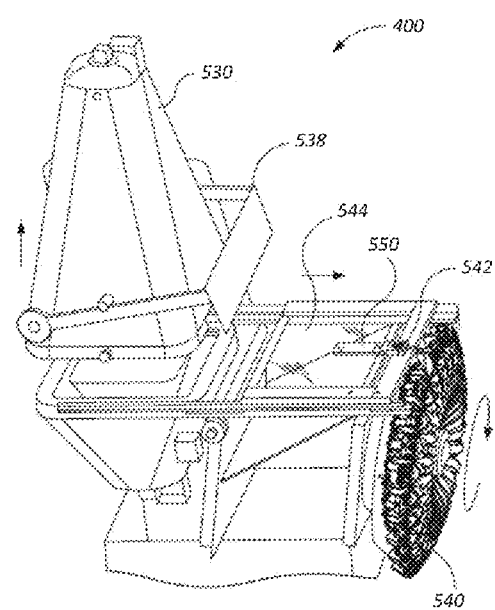
Figure 5D:
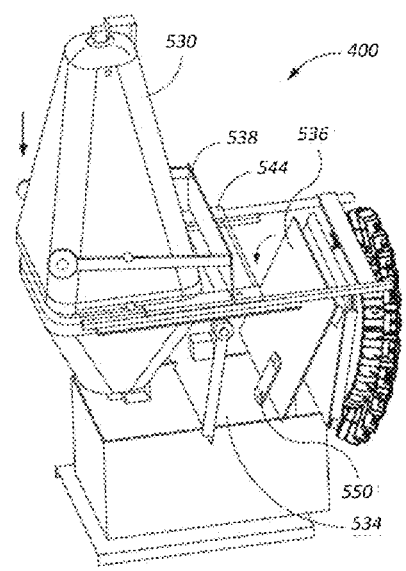

Referring next to FIG. 5C, after the visual analysis is performed and the device has been identified, the upper chamber 530 returns to its upper position and the transparent plate 544 returns the mobile phone 550 to its initial position near the door 406. The display screen 404 can also provide an estimated price, or an estimated range of prices, that the kiosk 400 may offer the user for the mobile phone 550 based on the visual analysis, and/or based on user input (e.g., input regarding the type, condition, etc. of the phone 550). If the user indicates (via, e.g., input via the touch screen) that they wish to proceed with the transaction, the connector carrier 540 automatically rotates an appropriate one of the connectors 542 into position adjacent the transparent plate 544, and door 406 is again opened. The user can then be instructed (via, e.g., the display screen 404) to withdraw the selected connector 542 (and its associated wire) from the carrousel 540, plug the connector 542 into the corresponding port (e.g., a USB port) on the mobile phone 550, and reposition the mobile phone 550 in the inspection area on the transparent plate 544. After doing so, the door 406 once again closes and the kiosk 400 (e.g. the kiosk CPU) performs an electrical inspection of the device via the connector 542 to further evaluate the condition of the phone as well as specific component and operating parameters such as the memory, carrier, etc. In addition or alternatively, in some embodiments the electrical inspection can include a determination of phone manufacturer information (e.g., a vendor identification number or VID) and product information (e.g., a product identification number or PID). In some embodiments, the kiosk 400 can perform the electrical analysis using one or more of the methods and/or systems described in detail in the commonly owned patents and patent applications identified herein and incorporated by reference in their entireties.

After the visual and electronic analysis of the mobile phone 550, the user is presented with a phone purchase price via the display screen 404. If the user declines the price (via, e.g., the touch screen), a retraction mechanism (not shown) automatically disconnects the connector 542 from the mobile phone 550, the door 406 opens, and the user can reach in and retrieve the mobile phone 550. If the user accepts the price, the door 406 remains closed and the user may be prompted to place his or her identification (e.g., a driver's license) in the ID scanner 412 and provide a thumbprint via the fingerprint reader 414. As a fraud prevention measure, the kiosk 400 can be configured to transmit an image of the driver's license to a remote computer screen, and an operator at the remote computer can visually compare the picture (and/or other information) on the driver's license to an image of the person standing in front of the kiosk 400 as viewed by one or more of the cameras 416a-c (FIG. 4) to confirm that the person attempting to sell the phone 550 is in fact the person identified by the driver's license. In some embodiments, one or more of the cameras 416a-c can be movable to facilitate viewing of kiosk users, as well as other individuals in the proximity of the kiosk 400. Additionally, the person's fingerprint can be checked against records of known fraud perpetrators. If either of these checks indicate that the person selling the phone presents a fraud risk, the transaction can be declined and the mobile phone 550 returned. After the user's identity has been verified, the transparent plate 544 moves back toward the upper and lower chambers 530 and 532. As shown in FIG. 5D, however, when the upper chamber 530 is in the lower position the gate 538 permits the transparent plate 544 to slide underneath but not electronic devices carried thereon. As a result, the gate 538 knocks the mobile phone 550 off of the transparent plate 544, onto the binning plate 536 and into the bin 534. The kiosk can then provide payment of the purchase price to the user. In some embodiments, payment can be made in the form of cash dispensed from the cash outlet 418. In other embodiments, the user can receive remuneration for the mobile phone 550 in various other useful ways. For example, the user can be paid via a redeemable cash voucher, a coupon, an e-certificate, a prepaid card, a wired or wireless monetary deposit to an electronic account (e.g., a bank account, credit account, loyalty account, online commerce account, mobile wallet etc.), Bitcoin, etc.

As those of ordinary skill in the art will appreciate, the foregoing routines are but some examples of ways in which the kiosk 400 can be used to recycle or otherwise process consumer electronic devices such as mobile phones. Although the foregoing example is described in the context of mobile phones, it should be understood that the kiosk 400 and various embodiments thereof can also be used in a similar manner for recycling virtually any consumer electronic device, such as MP3 players, tablet computers, PDAs, and other portable devices, as well as other relatively non-portable electronic devices such as desktop computers, printers, devices for implementing games, entertainment or other digital media on CDs, DVDs, Blu-ray, etc. Moreover, although the foregoing example is described in the context of use by a consumer, the kiosk 400 in various embodiments thereof can similarly be used by others, such as a store clerk, to assist consumers in recycling, selling, exchanging, etc. their electronic devices.

The disclosed technology also includes the disclosures of U.S. patent application Ser. No. 14/498,763, titled "METHODS AND SYSTEMS FOR PRICING AND PERFORMING OTHER PROCESSES ASSOCIATED WITH RECYCLING MOBILE PHONES AND OTHER ELECTRONIC DEVICES," filed by the applicant on Sep. 26, 2014; U.S. patent application Ser. No. 14/500,739, titled "MAINTAINING SETS OF CABLE COMPONENTS USED FOR WIRED ANALYSIS, CHARGING, OR OTHER INTERACTION WITH PORTABLE ELECTRONIC DEVICES," filed by the applicant on Sep. 29, 2014; U.S. patent application Ser. No. 14/873,158, titled "WIRELESS-ENABLED KIOSK FOR RECYCLING CONSUMER DEVICES," filed by the applicant on Oct. 1, 2015; U.S. patent application Ser. No. 14/873,145, titled "APPLICATION FOR DEVICE EVALUATION AND OTHER PROCESSES ASSOCIATED WITH DEVICE RECYCLING," filed by the applicant on Oct. 1, 2015; U.S. patent application Ser. No. 14/506,449, titled "SYSTEM FOR ELECTRICALLY TESTING MOBILE DEVICES AT A CONSUMER-OPERATED KIOSK, AND ASSOCIATED DEVICES AND METHODS," filed by the applicant on Oct. 3, 2014; U.S.

patent application Ser. No. 14/925,357, titled "SYSTEMS AND METHODS FOR RECYCLING CONSUMER ELECTRONIC DEVICES," U.S. patent application Ser. No. 14/925,375, titled "METHODS AND SYSTEMS FOR FACILITATING PROCESSES ASSOCIATED WITH INSURANCE SERVICES AND/OR OTHER SERVICES FOR ELECTRONIC DEVICES," filed by the applicant on Oct. 28, 2015; U.S. patent application Ser. No. 14/964,963, titled "METHODS AND SYSTEMS FOR PROVIDING INFORMATION REGARDING COUPONS/PROMOTIONS AT KIOSKS FOR RECYCLING MOBILE PHONES AND OTHER ELECTRONIC DEVICES," filed by the applicant on Dec. 10, 2015; U.S. patent application Ser. No. 14/568,051, titled "METHODS AND SYSTEMS FOR IDENTIFYING MOBILE PHONES AND OTHER ELECTRONIC DEVICES," filed by the applicant on Dec. 11, 2014; U.S. patent application Ser. No. 14/966,346, titled "SYSTEMS AND METHODS FOR RECYCLING CONSUMER ELECTRONIC DEVICES," filed by the applicant on Dec. 11, 2015; U.S. patent application Ser. No. 14/598,469, titled "METHODS AND SYSTEMS FOR DYNAMIC PRICING AND PERFORMING OTHER PROCESSES ASSOCIATED WITH RECYCLING MOBILE PHONES AND OTHER ELECTRONIC DEVICES," filed by the applicant on Jan. 16, 2015; U.S. patent application Ser. No. 14/660,768, titled "SYSTEMS AND METHODS FOR INSPECTING MOBILE DEVICES AND OTHER CONSUMER ELECTRONIC DEVICES WITH A LASER," filed by the applicant on Mar. 17, 2015; U.S. patent application Ser. No. 14/663,331, titled "DEVICE RECYCLING SYSTEMS WITH FACIAL RECOGNITION," filed by the applicant on Mar. 19, 2015; U.S. provisional application No. 62/169,072, titled "METHODS AND SYSTEMS FOR VISUALLY EVALUATING ELECTRONIC DEVICES," filed by the applicant on Jun. 1, 2015; U.S. provisional application No. 62/202,330, titled "METHODS AND SYSTEMS FOR INSPECTING MOBILE DEVICES AND OTHER CONSUMER ELECTRONIC DEVICES WITH ROBOTIC ACTUATION," filed by the applicant on Aug. 7, 2015; U.S. patent application Ser. No. 15/057,707, titled "METHODS AND SYSTEMS FOR RECORDING INTERACTIONS WITH A SYSTEM FOR PURCHASING MOBILE PHONES AND OTHER ELECTRONIC DEVICES," filed by the applicant on Mar. 1, 2016; U.S. patent application Ser. No. 14/873,158, titled "WIRELESS-ENABLED KIOSK FOR RECYCLING CONSUMER DEVICES," filed by the applicant on Oct. 1, 2015; U.S. patent application Ser. No. 14/873,145, titled "APPLICATION FOR DEVICE EVALUATION AND OTHER PROCESSES ASSOCIATED WITH DEVICE RECYCLING," filed by the applicant on Oct. 1, 2015; U.S. patent application Ser. No. 14/925,357, titled "SYSTEMS AND METHODS FOR RECYCLING CONSUMER ELECTRONIC DEVICES," filed by the applicant on Oct. 28, 2015; U.S. patent application Ser. No. 14/925,375, titled "METHODS AND SYSTEMS FOR FACILITATING PROCESSES ASSOCIATED WITH INSURANCE SERVICES AND/OR OTHER SERVICES FOR ELECTRONIC DEVICES," filed by the applicant on Oct. 28, 2015; U.S. patent application Ser. No. 14/934,134, titled "METHODS AND SYSTEMS FOR EVALUATING AND RECYCLING ELECTRONIC DEVICES," and U.S. patent application Ser. No. 14/967,183, titled "SYSTEMS AND METHODS FOR RECYCLING CONSUMER ELECTRONIC DEVICES," filed Dec. 11, 2015, each of which is incorporated herein by reference in its entirety. All of the patents and patent applications listed above are commonly owned by the applicant of the present application, and they along with any other patents or patent applications identified herein are incorporated herein by reference in their entireties.

While the Internet is shown, a private network, such as an intranet may likewise be used herein. The network may have a client-server architecture, in which a computer is dedicated to serving other client computers, or it may have other architectures such as peer-to-peer, in which one or more computers serve simultaneously as servers and clients. A database or databases, coupled to the server computer(s), stores much of the web pages and content exchanged between the user computers. The server computer(s), including the database(s), may employ security measures to inhibit malicious attacks on the system and preserve the integrity of the messages and data stored therein (e.g., firewall systems, message encryption and/or authentication (e.g., using transport layer security (TLS) or secure socket layers (SSL)), password protection schemes, encryption of stored data (e.g., using trusted computing hardware), and the like).

One skilled in the relevant art will appreciate that the concepts of the invention can be used in various environments other than location based or the Internet. In general, a display description may be in HTML, XML or WAP format, email format or any other format suitable for displaying information (including character/code-based formats, algorithm-based formats (e.g., vector generated), and bitmapped formats). Also, various communication channels, such as local area networks, wide area networks, or point-to-point dial-up connections, may be used instead of the Internet. The system may be conducted within a single computer environment, rather than a client/server environment. Also, the user computers may comprise any combination of hardware or software that interacts with the server computer, such as television-based systems and various other consumer products through which commercial or noncommercial transactions can be conducted. The various aspects of the invention described herein can be implemented in or for any e-mail environment.

Although not required, aspects of the invention are described in the general context of computer-executable instructions, such as routines executed by a general-purpose data processing device, e.g., a server computer, wireless device or personal computer. Those skilled in the relevant art will appreciate that aspects of the invention can be practiced with other communications, data processing, or computer system configurations, including Internet appliances, hand-held devices (including personal digital assistants (PDAs)), wearable computers, all manner of cellular or mobile phones (including Voice over IP (VoIP) phones), dumb terminals, media players, gaming devices, multi-processor systems, microprocessor-based or programmable consumer electronics, set-top boxes, network PCs, mini-computers, mainframe computers, and the like. Indeed, the terms "computer," "server," "host," "host system," and the like, are generally used interchangeably herein, and refer to any of the above devices and systems, as well as any data processor. Input devices may include a touchpad, keyboard and/or a pointing device such as a mouse. Other input devices are possible such as a microphone, joystick, pen, game pad, scanner, digital camera, video camera, and the like. The data storage devices may include any type of computer-readable media that can store data accessible by a computer, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to a network such as a local area network (LAN), wide area network (WAN) or the Internet.

Aspects of the invention can be embodied in a special purpose computer or data processor that is specifically programmed, configured, or constructed to perform one or more of the computer-executable instructions explained in detail herein. While aspects of the invention, such as certain functions, are described as being performed exclusively on a single device, the invention can also be practiced in distributed environments where functions or modules are shared among disparate processing devices, which are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. The data storage devices may include any type of computer-readable media that can store data accessible by a computer, such as magnetic hard and floppy disk drives, optical disk drives, magnetic cassettes, tape drives, flash memory cards, DVDs, Bernoulli cartridges, RAM, ROMs, smart cards, etc. Indeed, any medium for storing or transmitting computer-readable instructions and data may be employed, including a connection port to a network such as a LAN, WAN, or the Internet. Alternatively, computer implemented instructions, data structures, screen displays, and other data under aspects of the invention may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). The terms "memory" and "computer-readable storage medium" include any combination of temporary, persistent, and/or permanent storage, e.g., ROM, writable memory such as RAM, writable non-volatile memory such as flash memory, hard drives, solid state drives, removable media, and so forth, but do not include a propagating signal per se.

The above Detailed Description of examples and embodiments of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

Unless the context clearly requires otherwise, throughout the description and the claims, the words "comprise," "comprising," and the like, are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples—alternative implementations may employ differing values or ranges.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention. Accordingly, the invention is not limited, except as by the appended claims. Although certain aspects of the invention are presented below in certain claim forms, the applicant contemplates the various aspects of the invention in any number of claim forms. Accordingly, the applicant reserves the right to pursue additional claims after filing this application to pursue such additional claim forms, in either this application or in a continuing application.

We claim:

1. A method performed by one or more computing devices for detecting cracks in an electronic device, the method comprising:
   receiving an image of an electronic device;
   automatically identifying a plurality of edges in the image;
   for individual edges among the identified edges, determining whether another edge among the identified edges is present within a predetermined distance of each of the individual edges;
   automatically identifying straight line segments corresponding to the individual edges for which another edge is within the predetermined distance; and
   evaluating a condition of the electronic device based at least in part on the number of identified straight line segments.

2. The method of claim 1 wherein:
   automatically identifying the straight line segments includes applying a Hough line transform to the edges for which another edge is within the predetermined distance, and
   evaluating a condition of the electronic device includes assigning the crack evaluation assessment based at least in part on a result of applying the Hough line transform.

3. The method of claim 1 wherein determining, respectively, whether another edge among the identified edges is present within the predetermined distance comprises:
   for a given point along an individual edge among the identified edges:
      determining whether another edge among the identified edges is present within a first predetermined distance along a first axis; and
      determining whether another edge among the identified edges is present within a second predetermined distance along a second axis orthogonal to the first axis.

4. The method of claim 1 wherein automatically identifying the edges comprises applying a Canny edge detector to the image.

5. The method of claim 1 wherein the image is of a screen and a non-screen portion of the electronic device, and wherein the method further comprises applying a first filter to the screen portion and applying a second filter to the non-screen portion before automatically identifying the edges.

6. The method of claim 1 wherein the predetermined distance is not more than about 1.5 mm.

7. The method of claim 1 wherein evaluating a condition of the electronic device comprises calculating a number of pixels in the image that are included in the identified straight line segments.

8. The method of claim 1, further comprising determining a value for the electronic device based on the evaluated condition of the electronic device.

9. A method performed by one or more computing devices for detecting cracks in an electronic device, the method comprising:
   receiving an image of an electronic device;
   automatically identifying a plurality of edges in the image;
   automatically determining whether individual edges among the identified edges are within a pre-selected proximity to other individual edges among the identified edges; and
   assessing the condition of the electronic device based at least in part on the number of the edges within the pre-selected proximity to other edges.

10. The method of claim 9 wherein, in assessing the condition of the electronic device, the edges not within the pre-selected proximity to other edges have no weight.

11. The method of claim 9 wherein automatically determining whether individual edges among the identified edges are within a pre-selected proximity to other individual edges among the identified edges comprises:
   for an individual edge among the identified edges:
      determining whether another edge among the identified edges is present within a first predetermined distance along a first axis;
      determining whether another edge among the identified edges is present within a second predetermined distance along a second axis orthogonal to the first axis; and
      if another edge among the identified edges is present within the first predetermined distance along the first axis or within the second predetermined distance along the second axis, then indicating that the individual edge is within the pre-selected proximity to the other edge.

12. The method of claim 11 wherein the first predetermined distance is not more than about 1.5 mm.

13. The method of claim 9 wherein assessing the electronic device comprises calculating a number of pixels in the image that are included in the individual edges that are within the pre-selected proximity to other individual edges.

14. A method performed by one or more computing devices for detecting cracks in an electronic device, the method comprising:
   receiving an image of an electronic device;
   automatically identifying one or more edges in the image;
   identifying edge-to-non-edge-to-edge groupings among the identified edges; and
   assessing the condition of the electronic device based at least in part on the identified edge-to-non-edge-to-edge groupings, wherein, in the assessment, the edges in the identified edge-to-non-edge-to-edge groupings have greater weight than other edges among the identified edges.

15. The method of claim 14 wherein identifying edge-to-non-edge-to-edge groupings comprises:
   for an individual edge among the identified edges:
      determining whether another edge among the identified edges is present within a first predetermined distance along a first axis; and
      determining whether another edge among the identified edges is present within a second predetermined distance along a second axis orthogonal to the first axis.

16. The method of claim 14, wherein assessing the condition of the electronic device comprises calculating a number of pixels in the image that are included in the identified edge-to-non-edge-to-edge groupings.

17. A computer-readable memory carrying computer-executable instructions for causing one or more processors to facilitate detecting cracks in an electronic device, the computer-executable instructions comprising instructions that, when executed by the one or more processors:

receive an image of an electronic device;

automatically identify edges in the image;

for individual edges among the identified edges, determine whether another edge among the identified edges is present within a predetermined distance of the individual edge;

automatically identify straight line segments corresponding to the edges for which another edge is within the predetermined distance; and evaluate a condition of the electronic device based at least in part on the identified straight line segments.

18. The computer-readable memory of claim 17 wherein the computer-executable instructions, when executed by the one or more processors:

automatically identify the straight line segments at least in part by applying a Hough line transform to the edges for which another edge is within the predetermined distance; and evaluate the condition of the electronic device at least in part by assigning a crack evaluation assessment based at least in part on a result of applying the Hough line transform.

19. The computer-readable memory of claim 17 wherein the computer-executable instructions, when executed by the one or more processors, determine, respectively, whether another edge among the identified edges is present within the predetermined distance of an individual edge among the identified edges at least in part by:

for a given point along the individual edge:

determining whether another edge among the identified edges is present within a first predetermined distance along a first axis; and determining whether another edge among the identified edges is present within a second predetermined distance along a second axis orthogonal to the first axis.

20. The computer-readable memory of claim 17 wherein the computer-executable instructions, when executed by the one or more processors, automatically identify the straight line segments at least in part by applying a Canny edge detector to the image.

21. The computer-readable memory of claim 17 wherein the computer-executable instructions, when executed by the one or more processors, assign the crack evaluation assessment based at least in part on a number of pixels in the image that are included in the identified straight line segments.

* * * * *